(12) United States Patent
Luo et al.

(10) Patent No.: US 11,678,570 B2
(45) Date of Patent: Jun. 13, 2023

(54) HOLE TRANSPORT MATERIAL, PREPARATION METHOD THEREOF, AND ELECTROLUMINESCENT DEVICE

(71) Applicant: WUHAN CHINA STAR OPTOELECTRONICS SEMICONDUCTOR DISPLAY TECHNOLOGY CO., LTD., Wuhan (CN)

(72) Inventors: Jiajia Luo, Wuhan (CN); Munjae Lee, Wuhan (CN); Xianjie Li, Wuhan (CN); Xu Wang, Wuhan (CN); Kailong Wu, Wuhan (CN); Qu Zhang, Wuhan (CN)

(73) Assignee: WUHAN CHINA STAR OPTOELECTRONICS SEMICONDUCTOR DISPLAY TECHNOLOGY CO., LTD., Wuhan (CN)

( * ) Notice: Subject to any disclaimer, the term of this patent is extended or adjusted under 35 U.S.C. 154(b) by 447 days.

(21) Appl. No.: 16/755,571

(22) PCT Filed: Dec. 3, 2019

(86) PCT No.: PCT/CN2019/122714
§ 371 (c)(1),
(2) Date: Apr. 11, 2020

(87) PCT Pub. No.: WO2021/103058
PCT Pub. Date: Jun. 3, 2021

(65) Prior Publication Data
US 2021/0408389 A1  Dec. 30, 2021

(30) Foreign Application Priority Data
Nov. 25, 2019  (CN) .......................... 201911163611.7

(51) Int. Cl.
H01L 51/50 (2006.01)
H01L 51/00 (2006.01)
(Continued)

(52) U.S. Cl.
CPC ........ *H01L 51/0061* (2013.01); *B01D 15/426* (2013.01); *C07D 307/91* (2013.01);
(Continued)

(58) Field of Classification Search
None
See application file for complete search history.

(56) References Cited

U.S. PATENT DOCUMENTS

2016/0329507 A1  11/2016  Stoessel et al.

FOREIGN PATENT DOCUMENTS

| CN | 104203955 A | 12/2014 | |
| CN | 110382457 A * | 10/2015 | ............. H01L 51/50 |

(Continued)

*Primary Examiner* — Gregory D Clark
(74) *Attorney, Agent, or Firm* — PV IP PC; Wei Te Chung; Zhigang Ma

(57) ABSTRACT

The present invention provides a hole transport material, a preparation method thereof, and an electroluminescent device. Through ingenious molecular design, a xanthracene structure is combined with different electron-donating groups to synthesize a series of hole transport materials with a suitable highest occupied molecular orbital (HOMO) energy level and a suitable lowest unoccupied molecular orbital (LUMO) energy level, and a series of high-performance display devices can be manufactured using the hole transport materials provided by the present invention.

8 Claims, 1 Drawing Sheet

100
↓

| 10 |
| 9 |
| 8 |
| 7 |
| 6 |
| 5 |
| 4 |
| 3 |
| 2 |
| 1 |

(51) Int. Cl.
  *B01D 15/42*   (2006.01)
  *C07D 307/91*  (2006.01)
  *C07D 407/12*  (2006.01)
  *C09K 11/06*   (2006.01)
  *H01L 51/56*   (2006.01)

(52) U.S. Cl.
  CPC ............ *C07D 407/12* (2013.01); *C09K 11/06* (2013.01); *H01L 51/006* (2013.01); *C09K 2211/1018* (2013.01); *H01L 51/0007* (2013.01); *H01L 51/0026* (2013.01); *H01L 51/0052* (2013.01); *H01L 51/0056* (2013.01); *H01L 51/0073* (2013.01); *H01L 51/5056* (2013.01); *H01L 51/56* (2013.01); *H01L 2251/556* (2013.01)

(56) References Cited

FOREIGN PATENT DOCUMENTS

| | | | |
|---|---|---|---|
| CN | 106588674 | A | 4/2017 |
| CN | 109314189 | A | 2/2019 |
| CN | 109400486 | A | 3/2019 |
| CN | 109574858 | A | 4/2019 |
| CN | 109867652 | A | 6/2019 |
| CN | 110382457 | A | 10/2019 |
| CN | 110416422 | A | 11/2019 |
| KR | 20180136218 | A | 12/2018 |
| KR | 20190044974 | A | 5/2019 |
| KR | 20190114518 | A | 10/2019 |
| WO | 2018164265 | A1 | 9/2018 |
| WO | 2019088517 | A1 | 5/2019 |

\* cited by examiner

100
↓

| 10 |
|----|
| 9  |
| 8  |
| 7  |
| 6  |
| 5  |
| 4  |
| 3  |
| 2  |
| 1  |

HOLE TRANSPORT MATERIAL, PREPARATION METHOD THEREOF, AND ELECTROLUMINESCENT DEVICE

BACKGROUND OF INVENTION

Field of Invention

The present invention relates to a field of display technology, and in particular, to a hole transport material, a preparation method thereof, and an electroluminescent device.

Description of Prior Art

It is known that organic light-emitting diodes (OLEDs) have attracted attention from many researchers, due to their huge application prospects and advantages, such as self-illumination without the need for a backlight, high luminous efficiency, wide viewing angles, fast response speed, a large temperature adaptation range, relatively simple production and processing techniques, low driving voltage, low energy consumption, lightness, thinness, flexibility, and so on.

Guest luminescent materials for early OLEDs are fluorescent materials. Because the ratio of excitons in a singlet energy state and excitons in a triplet energy state in the OLED is 1:3, the theoretical internal quantum efficiency (IQE) of fluorescent-based OLEDs can merely reach 25%, thus considerably limiting the application of fluorescent electroluminescent devices. Heavy metal complex phosphorescent materials can achieve 100% IQE by using the excitons in the singlet energy state and the excitons in the triplet energy state due to a spin-orbit coupling of heavy atoms. However, heavy metals commonly employed are precious metals, such as Ir, Pt, and the like, and the heavy metal complex phosphorescent materials have yet to be developed in fields of blue light materials.

The currently used top-emitting OLED devices include the hole transport material as the thickest layer, and there has always been a contradiction between its energy level and hole mobility. Therefore, there is an urgent need to develop a hole transport material having a matched energy level and high mobility.

SUMMARY OF INVENTION

An object of the present invention is to provide a hole transport material, a preparation method thereof, and an electroluminescent device. Through ingenious molecular design, a xanthracene structure is combined with different electron-donating groups to synthesize a series of hole transport materials with a suitable highest occupied molecular orbital (HOMO) energy level and a suitable lowest unoccupied molecular orbital (LUMO) energy level, and a series of high-performance display devices can be manufactured using the hole transport materials provided by the present invention.

In order to achieve the above object, the present invention provides a hole transport material, hole transport material, including a compound consisting of a donor AN and an acceptor B, the compound having a general chemical structure as shown in Formula 1:

AN-BMN             Formula 1, wherein the donor AN is selected from any one of the following chemical structural formulas:

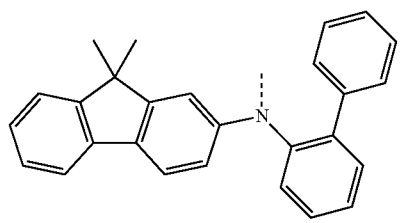

A1

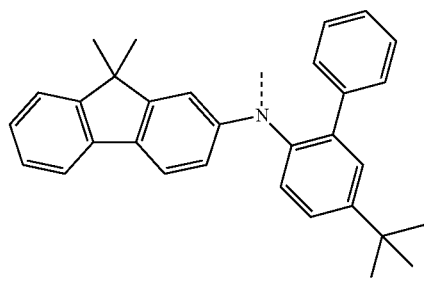

A2

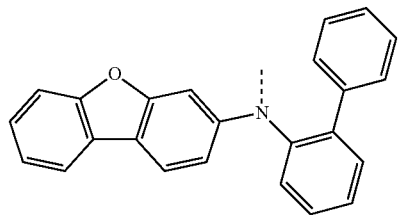

A3

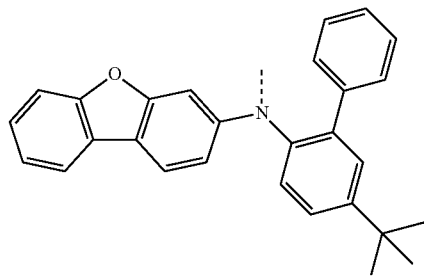

A4

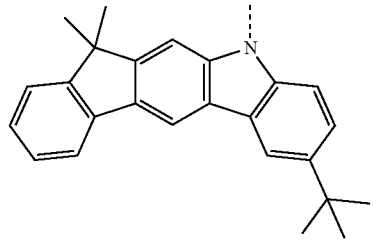

A5

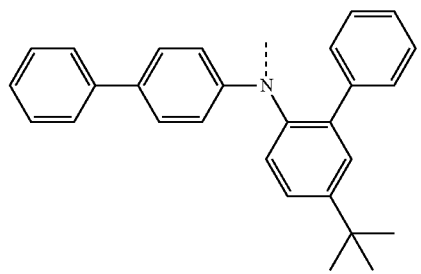

A6

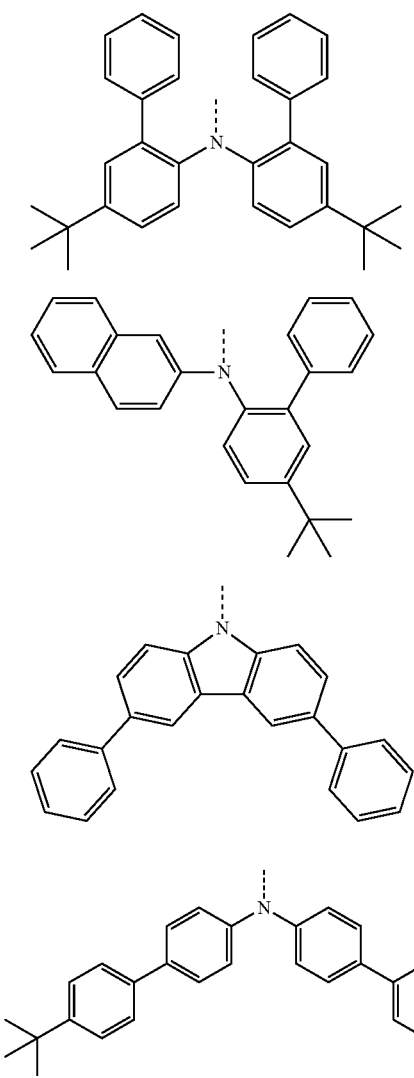
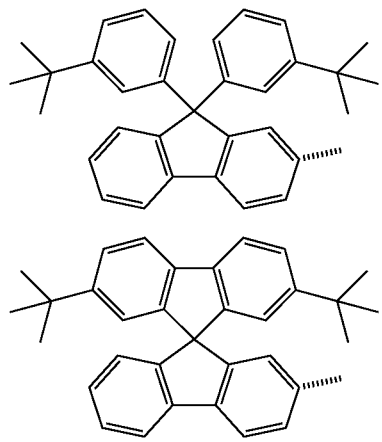
and
the acceptor BMN is selected from any one of the following chemical structural formulas:
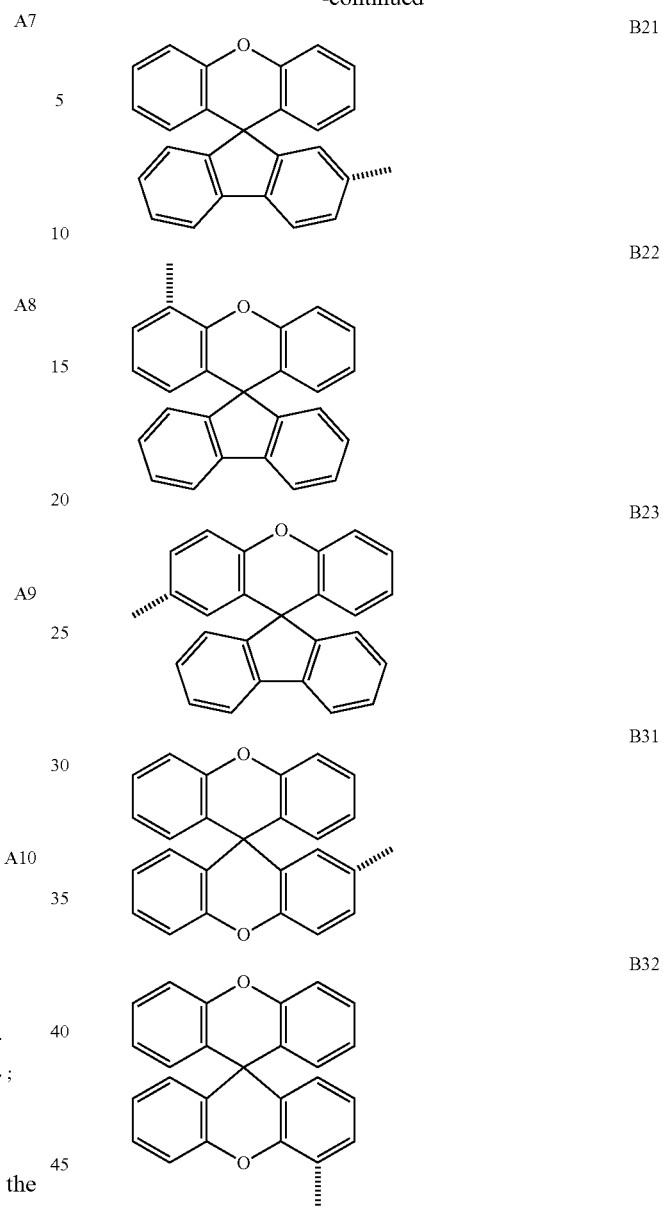

B43 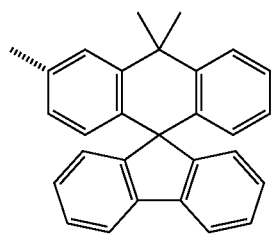
B44 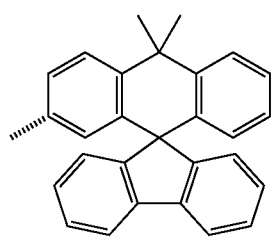
B51 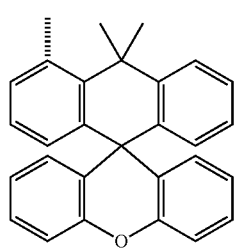
B52 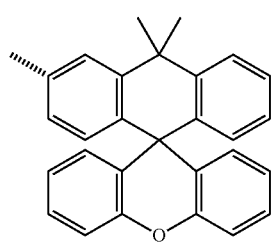
B53 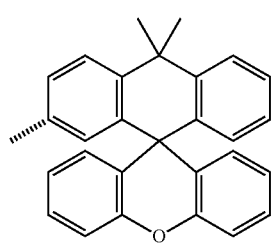
B54 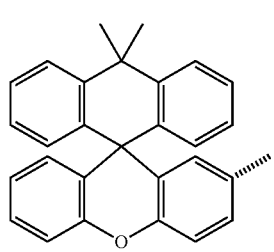
B55 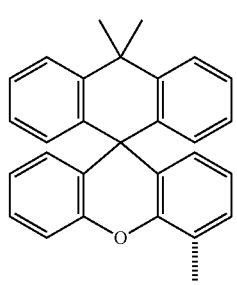
B61 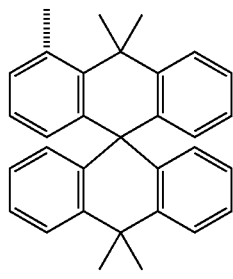
B62 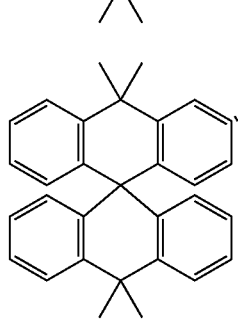
B63 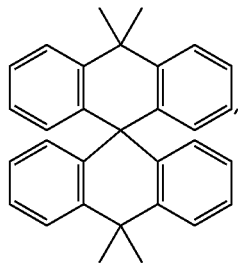
B71 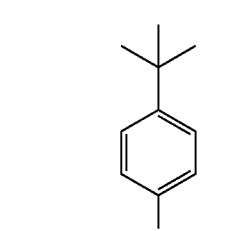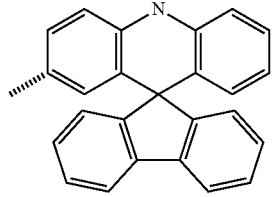

B72
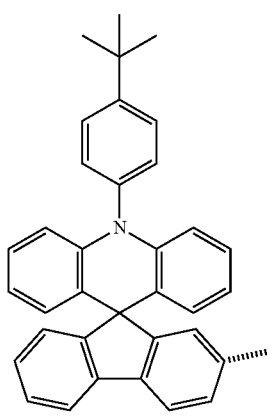
B81
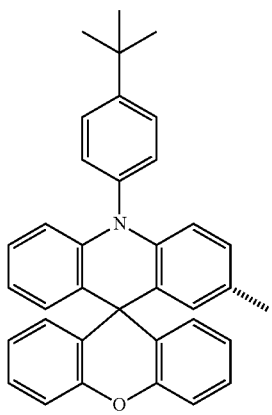
B82
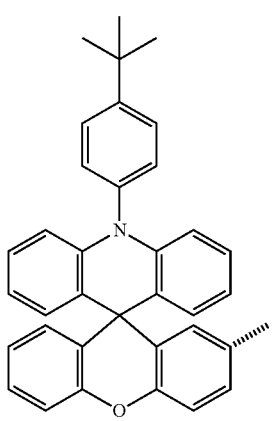
B83
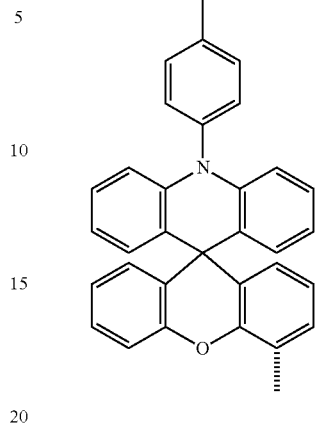
B91
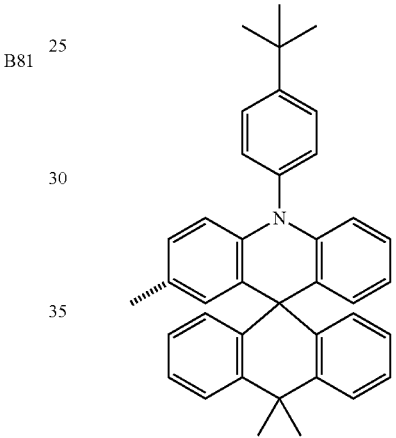
B92
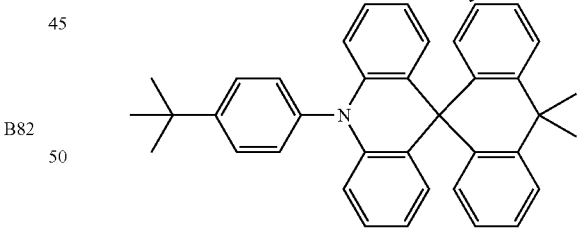
B93
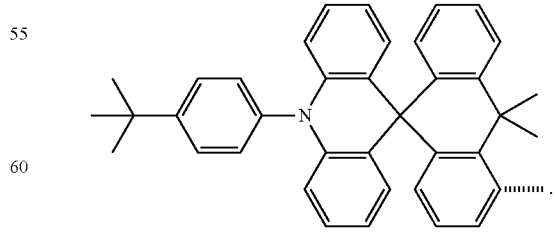
According to an embodiment of the present invention, the compound AN-BMN has any one of the following chemical structural formulas:

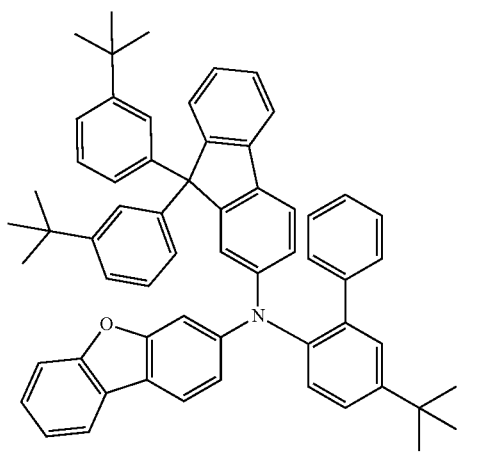

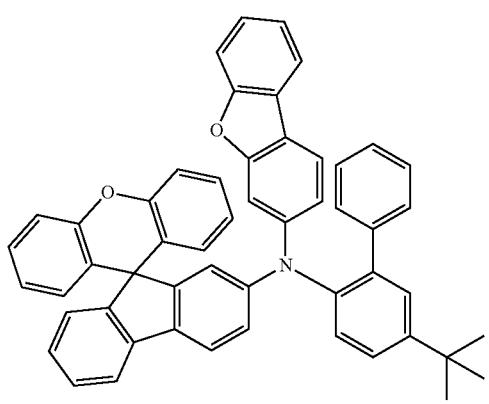

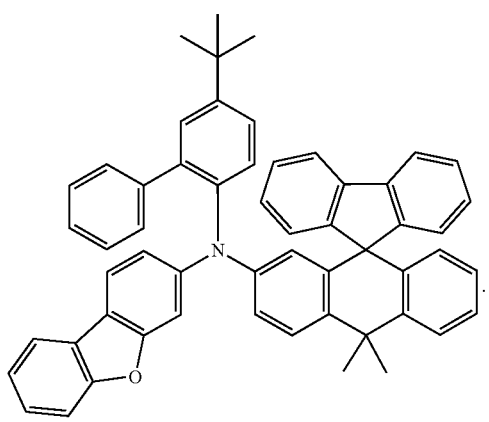

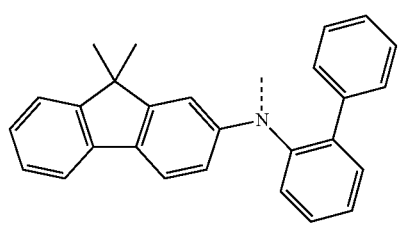

A1

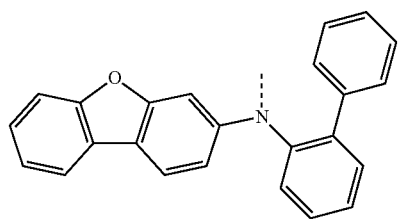

A2

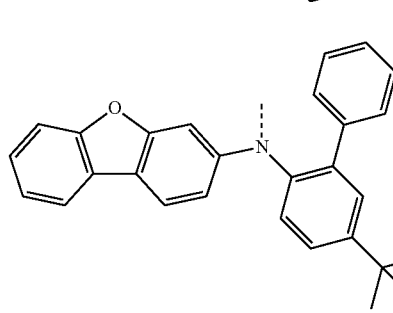

A3

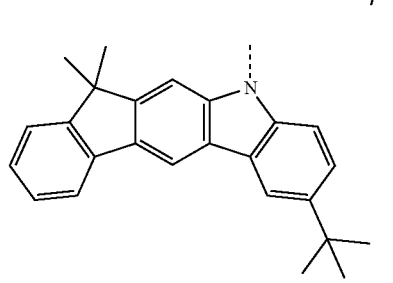

A4

A5

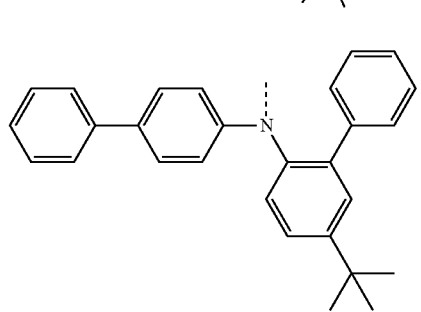

A6

According to another embodiment of the present invention, the present invention also provides a method of preparing a hole transport material, including the following steps:

Step S1, adding an acceptor compound BMN-X, a donor compound AN-H, and a catalyst into an organic solvent containing an alkali under an inert gas environment to conduct a reaction for a first time period at a first temperature to obtain a first reaction solution, wherein X is halogen, the donor AN is selected from any one of the following chemical structural formulas:

A7
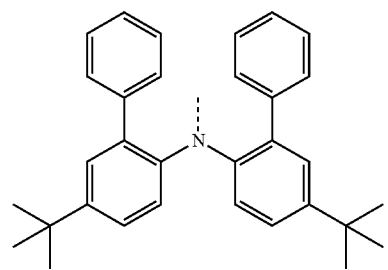
A8
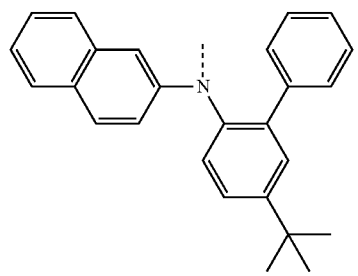
A9
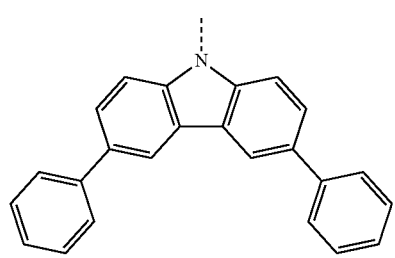
A10
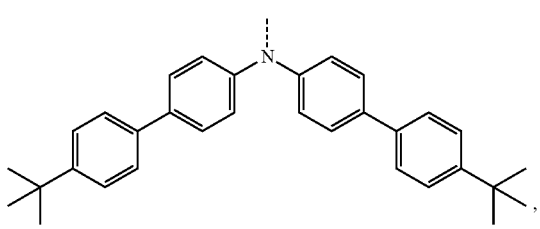
and the acceptor BMN is selected from any one of the following chemical structural formulas:
B11
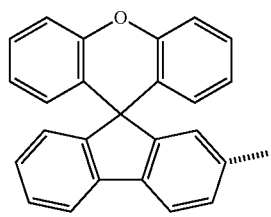
B12
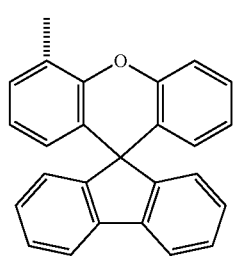
B21
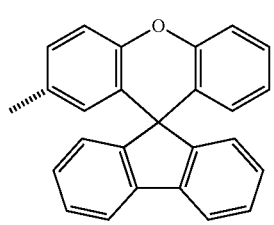
B22
B23
B31
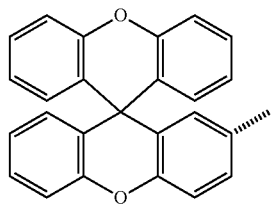
B32
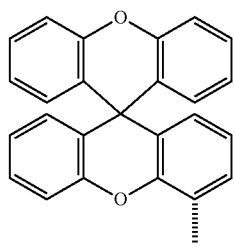
B41
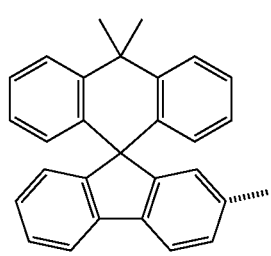

-continued
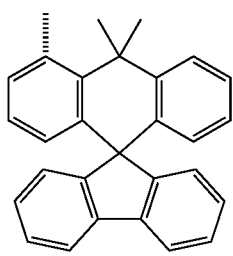
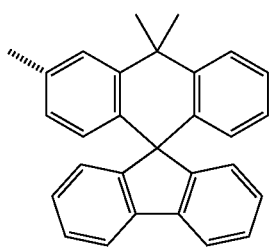
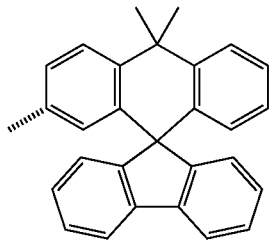
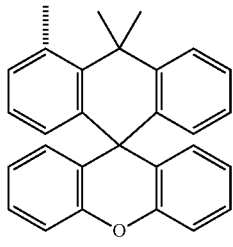
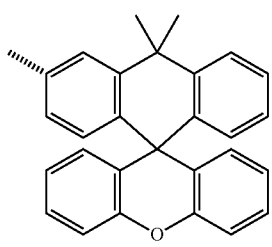
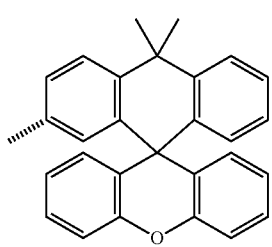
-continued
B42
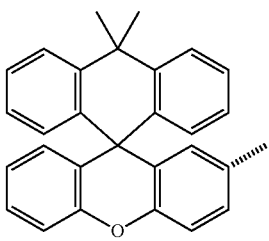
B43
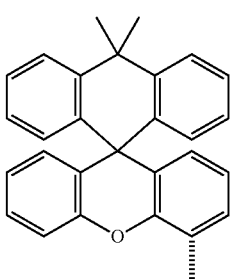
B44
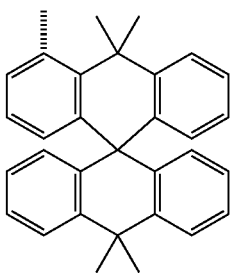
B51
B52
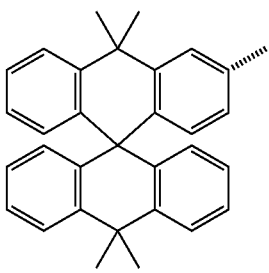
B53
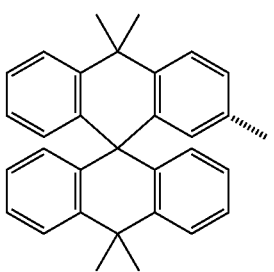
B54
B55
B61
B62
B63

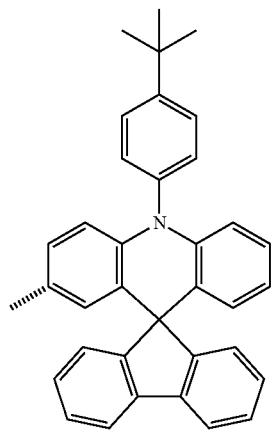
B71
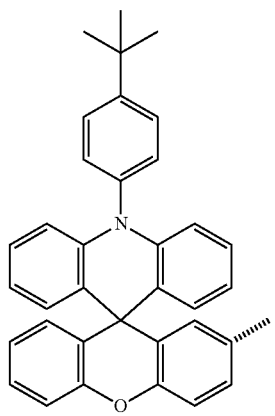
B82
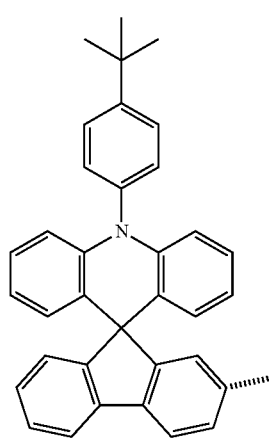
B72
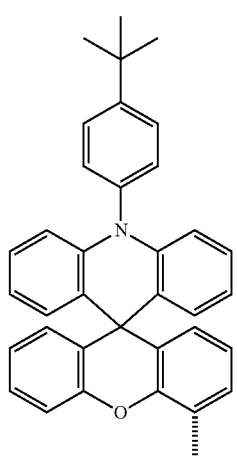
B83
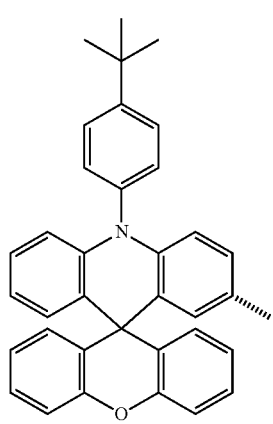
B81
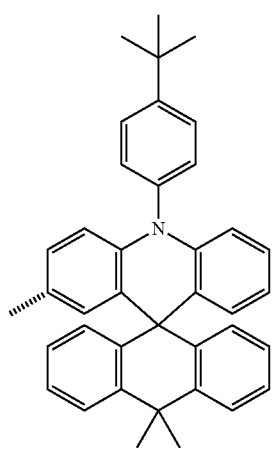
B91
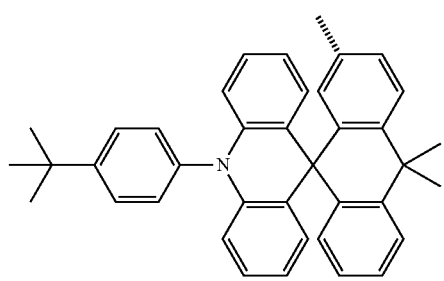
B92

-continued

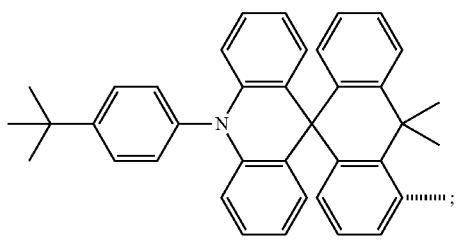

B93

Step S2, cooling the first reaction solution to a second temperature to obtain a mixture; and Step S3, separating the hole transport material from the mixture, the hole transport material including a compound having a general chemical structural formula shown in Formula 1:

AN-BMN                                        Formula 1.

According to an embodiment of the present invention, the first temperature ranges from 80° C. to 150° C., and the first time period ranges from 12 hours to 36 hours.

According to an embodiment of the present invention, the second temperature is room temperature.

According to an embodiment of the present invention, in the step S1, the organic solvent is toluene, the alkali is sodium tert-pentyloxylate, and the catalyst includes a palladium catalyst and phosphine ligand catalyst.

According to an embodiment of the present invention, the step S2 further includes: subjecting the first reaction solution to extraction, water washing, dehydration, filtration, and centrifugal drying to obtain the mixture.

According to an embodiment of the present invention, in the step S3, the separating is performed by column chromatography with an eluent of dichloromethane and n-hexane in a volume ratio of 1:3.

According to an embodiment of the present invention, in the step S1, the catalyst includes palladium acetate and tri-tert-butylphosphine tetrafluoroborate, and the compound AN-BMN has any one of the following chemical structural formulas:

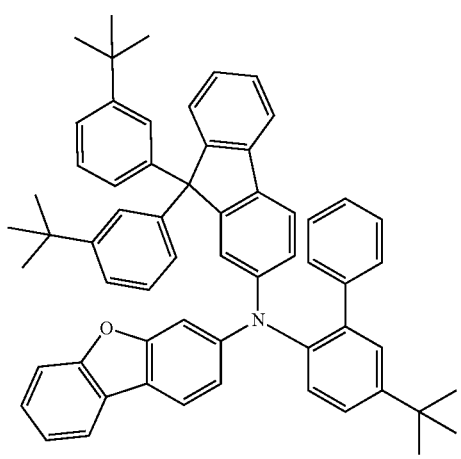

-continued

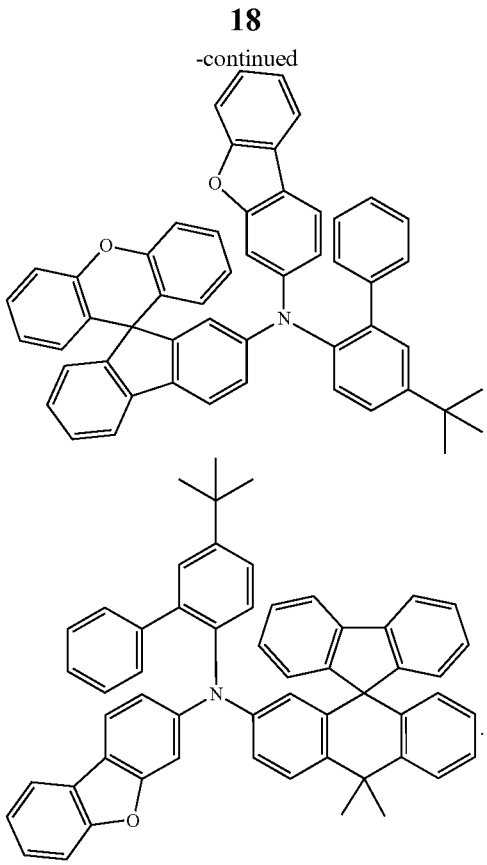

According to yet another embodiment of the present invention, the present invention further provides an electroluminescent device, including: a substrate; a hole injection layer disposed on the substrate; a hole transport layer disposed on the injection layer; an electron blocking layer disposed on the hole transport layer; a light-emitting layer disposed on the electron blocking layer; a hole blocking layer disposed on the light-emitting layer; an electron transport layer disposed on the hole blocking layer; an electron injection layer disposed on the electron transport layer; an electrode layer disposed on the electron injection layer; and a light-coupling output layer disposed on the electrode layer, wherein the hole transport layer includes the above-mentioned hole transport material.

An object of the present invention is to provide a hole transport material, a preparation method thereof, and an electroluminescent device. Through ingenious molecular design, a xanthracene structure is combined with different electron-donating groups to synthesize a series of hole transport materials with a suitable highest occupied molecular orbital (HOMO) energy level and a suitable lowest unoccupied molecular orbital (LUMO) energy level, and a series of high-performance display devices can be manufactured using the hole transport materials provided by the present invention.

BRIEF DESCRIPTION OF DRAWINGS

In order to more clearly illustrate the embodiments or the technical solutions of the existing art, the drawings illustrating the embodiments or the existing art will be briefly described below. Obviously, the drawings in the following description merely illustrate some embodiments of the pres- FIG. 1 is a schematic structural diagram of an electroluminescent device according to an embodiment of the present invention.

DETAILED DESCRIPTION OF PREFERRED EMBODIMENTS

In order to make the above description of the present invention more comprehensible, the preferred embodiments are described below in detail with reference to the accompanying drawings.

Embodiments of the present invention provide a hole transport material, a method of preparing the same, and an electroluminescent device. Through ingenious molecular design, a xanthracene structure is combined with different electron-donating groups to synthesize a series of hole transport materials with a suitable highest occupied molecular orbital (HOMO) energy level and a suitable lowest unoccupied molecular orbital (LUMO) energy level, and a series of high-performance display devices can be manufactured using the hole transport materials provided by the present invention.

In order to achieve the above object, the present invention provides a hole transport material, hole transport material, including a compound consisting of a donor AN and an acceptor B, the compound having a general chemical structure as shown in Formula 1:

AN-BMN          Formula 1,

A1
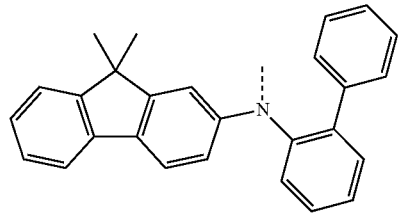

A2
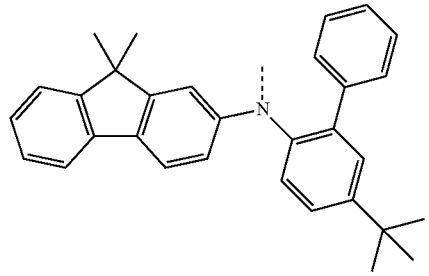

A3
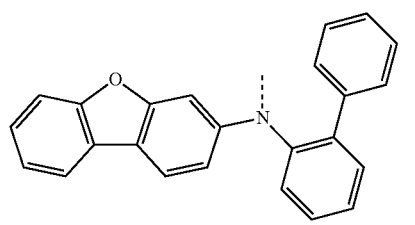

-continued

A4
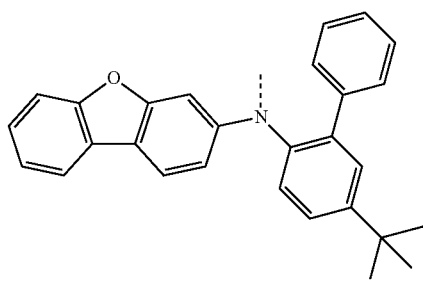

A5
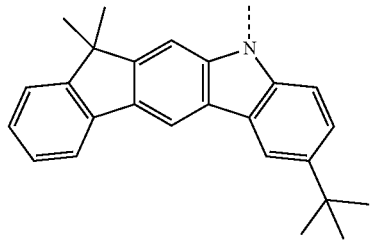

A6
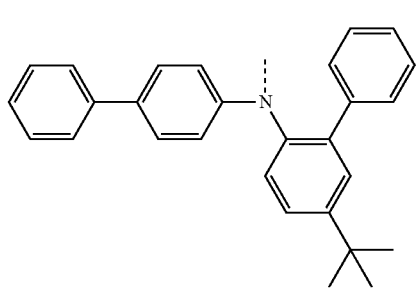

A7
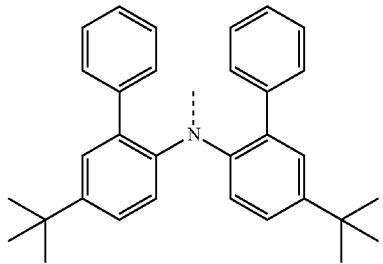

A8
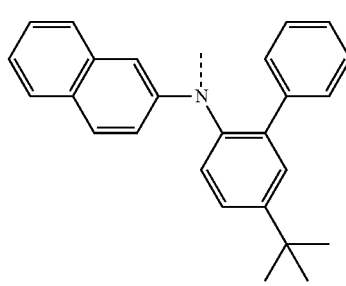

A9
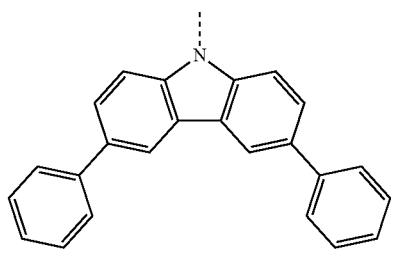

-continued
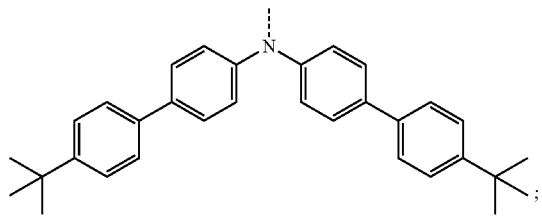
A10
and
the acceptor BMN is selected from any one of the following chemical structural formulas:
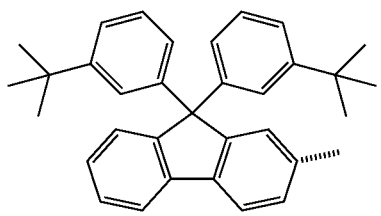
B11
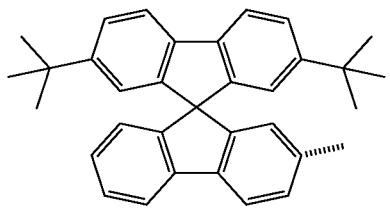
B12
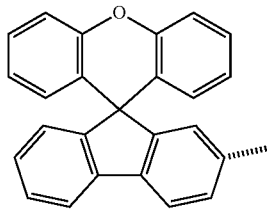
B21
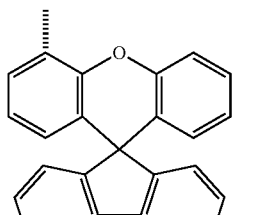
B22
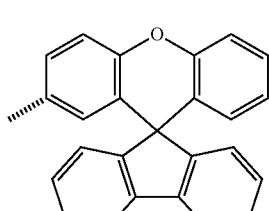
B23
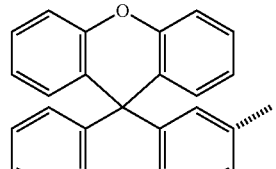
B31
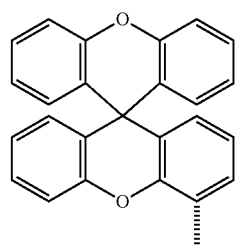
B32
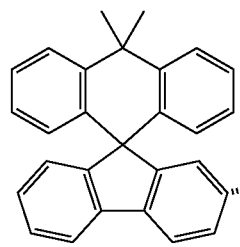
B41
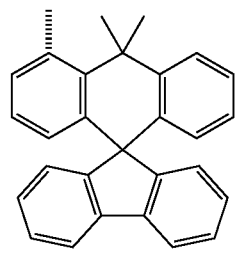
B42
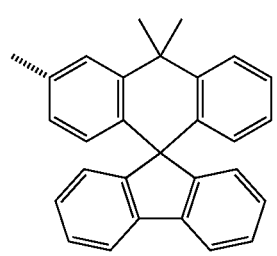
B43
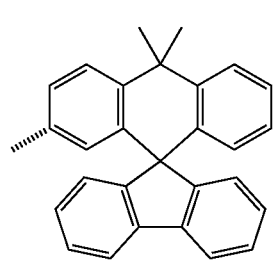
B44

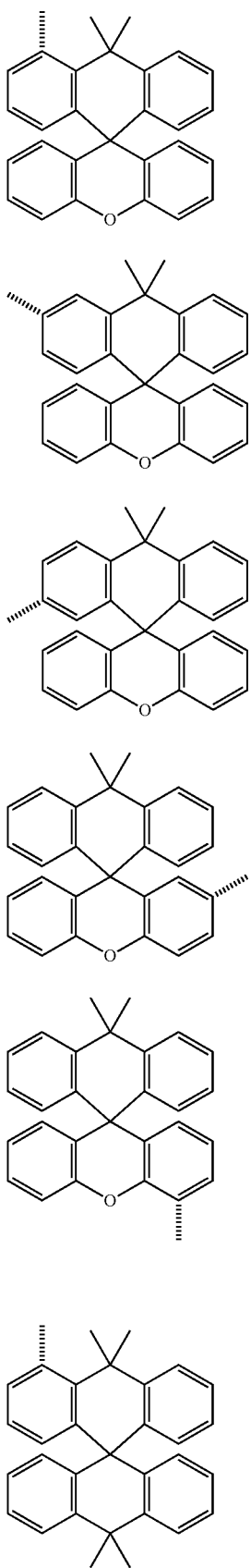
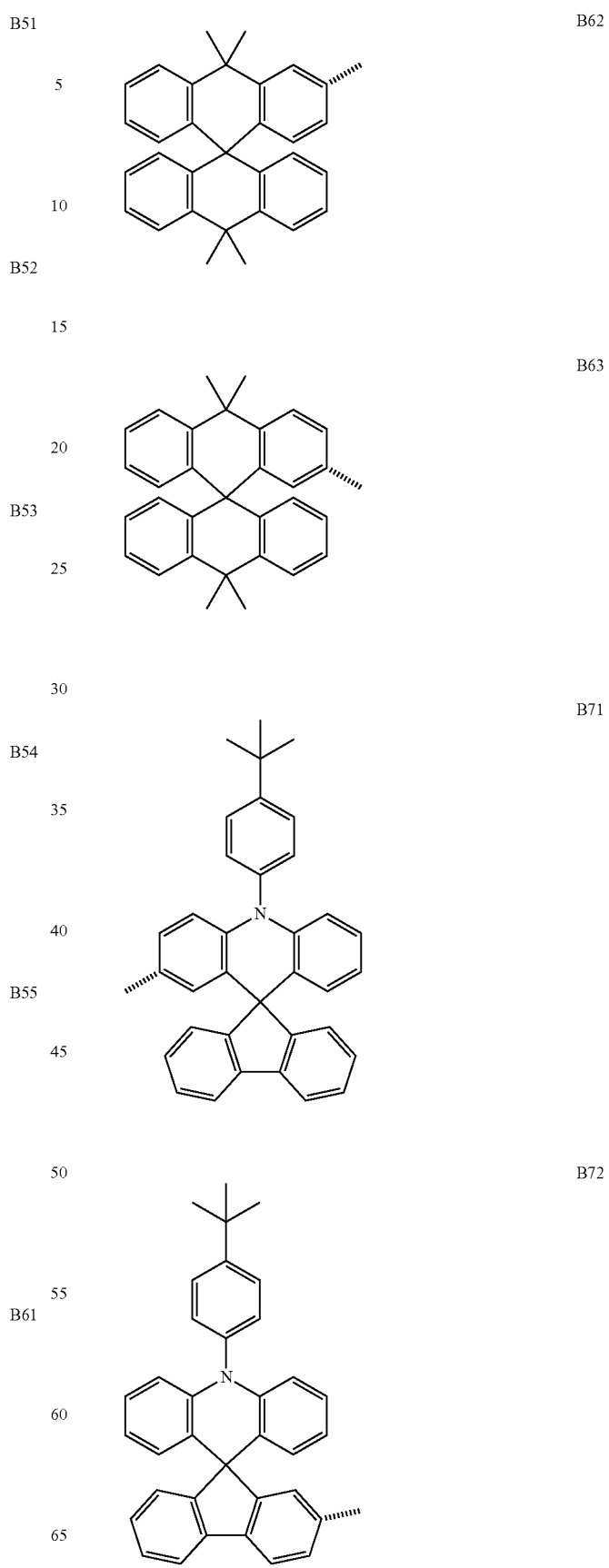

B81
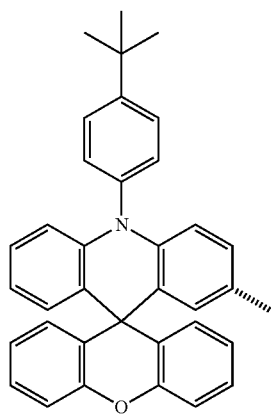
B82
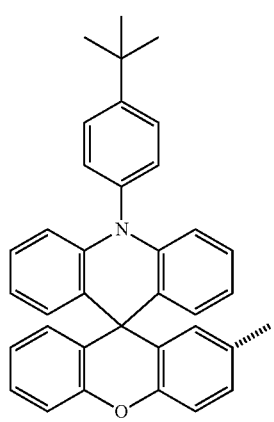
B83
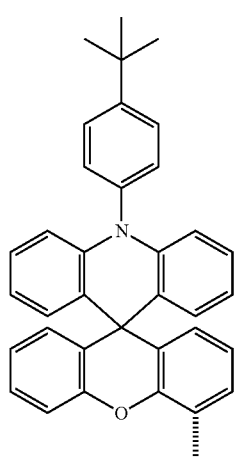
B91
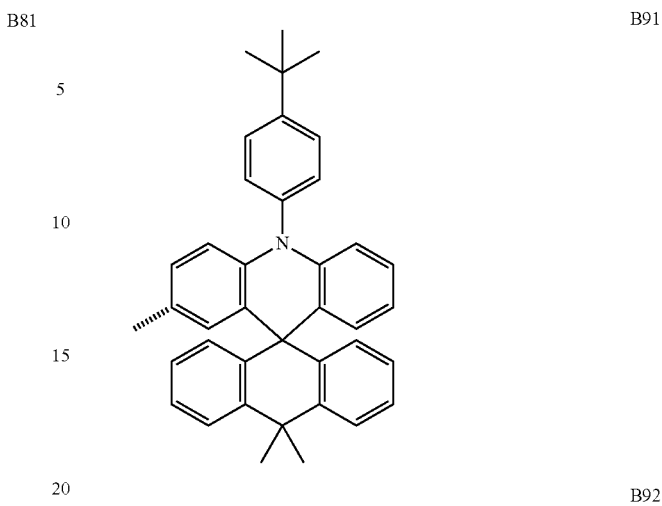
B92
B93
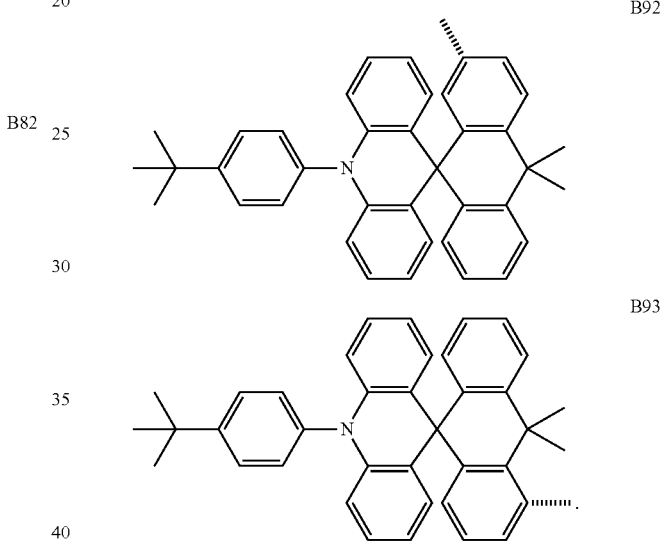
According to an embodiment of the present invention, the compound AN-BMN has any one of the following chemical structural formulas:
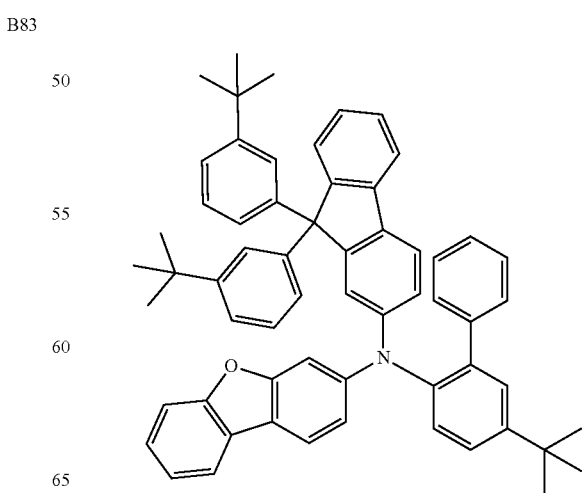

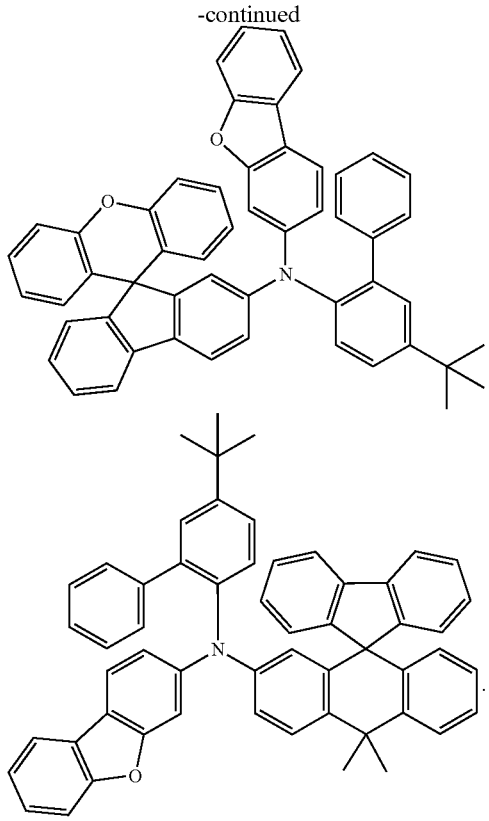

According to another embodiment of the present invention, the present invention also provides a method of preparing a hole transport material, including the following steps:

Step S1, adding an acceptor compound BMN-X, a donor compound AN-H, and a catalyst into an organic solvent containing an alkali under an inert gas environment to conduct a reaction for a first time period at a first temperature to obtain a first reaction solution, wherein X is halogen, the donor AN is selected from any one of the following chemical structural formulas:

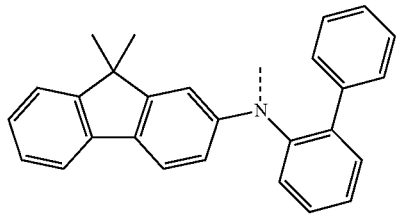

A1

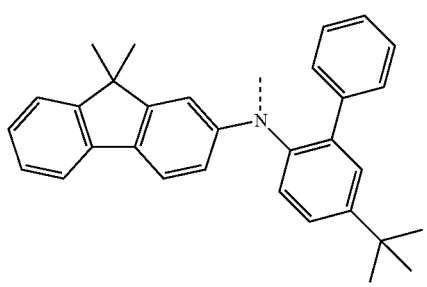

A2

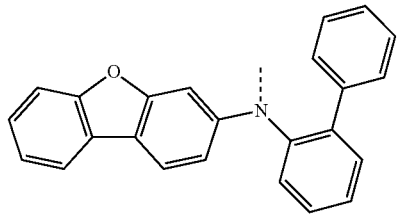

A3

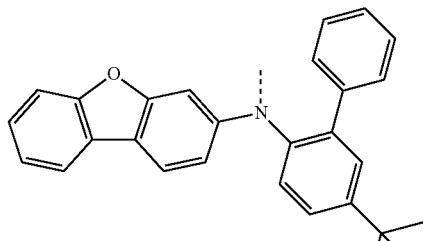

A4

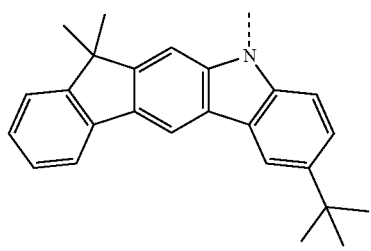

A5

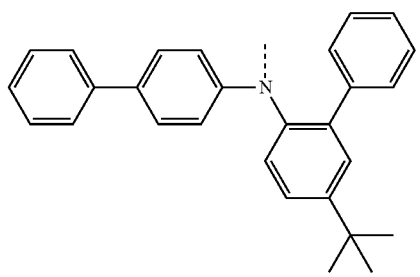

A6

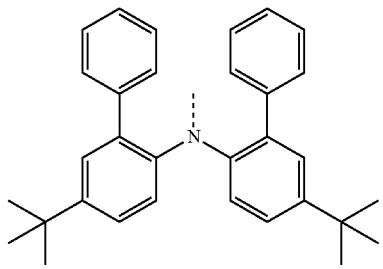

A7

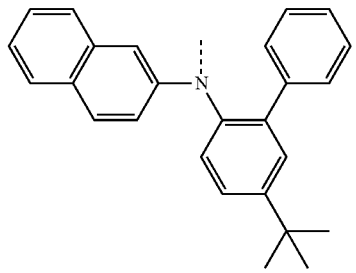

A8

A9
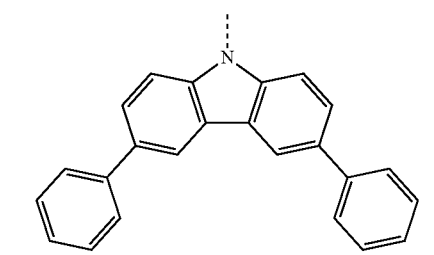
A10
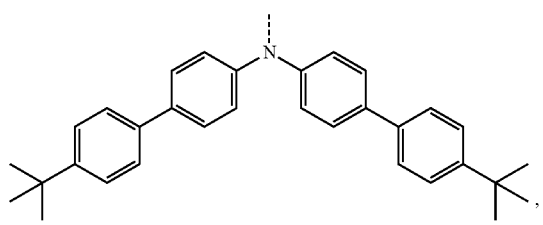
and the acceptor BMN is selected from any one of the following chemical structural formulas:
B11
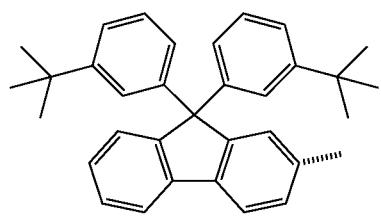
B12
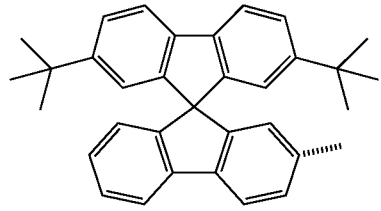
B21
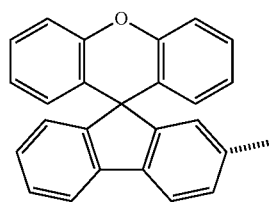
B22
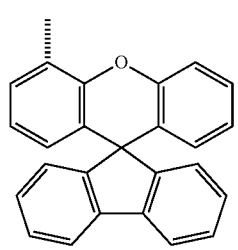
B23
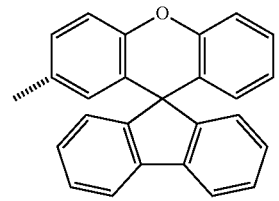
B31
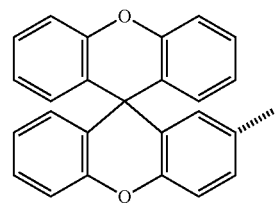
B32
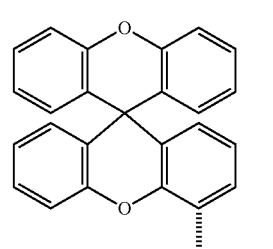
B41
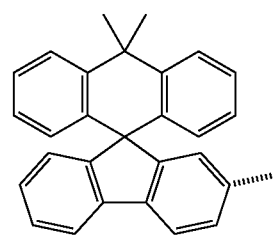
B42
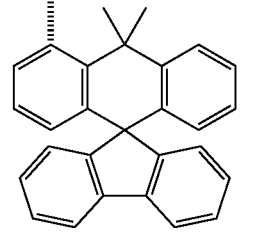
B43
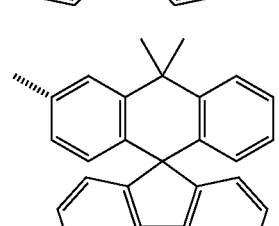
B44
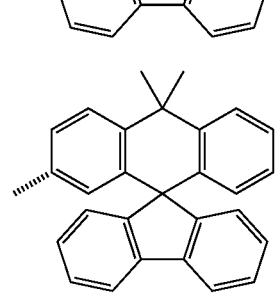

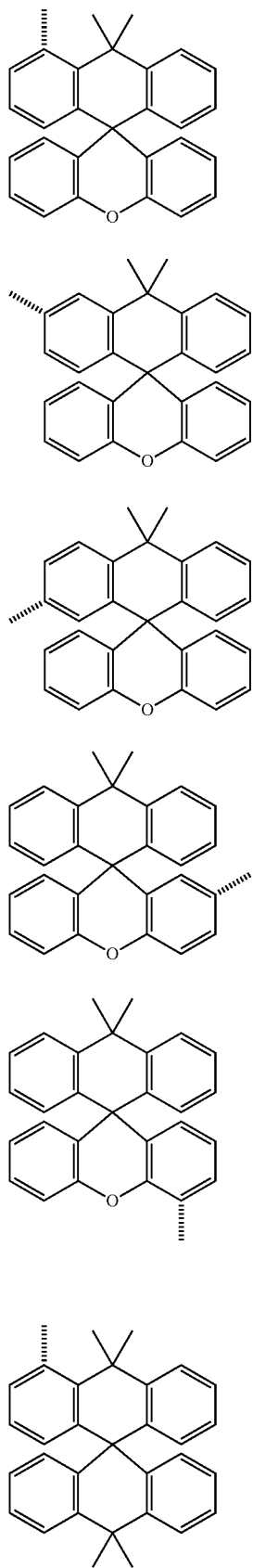
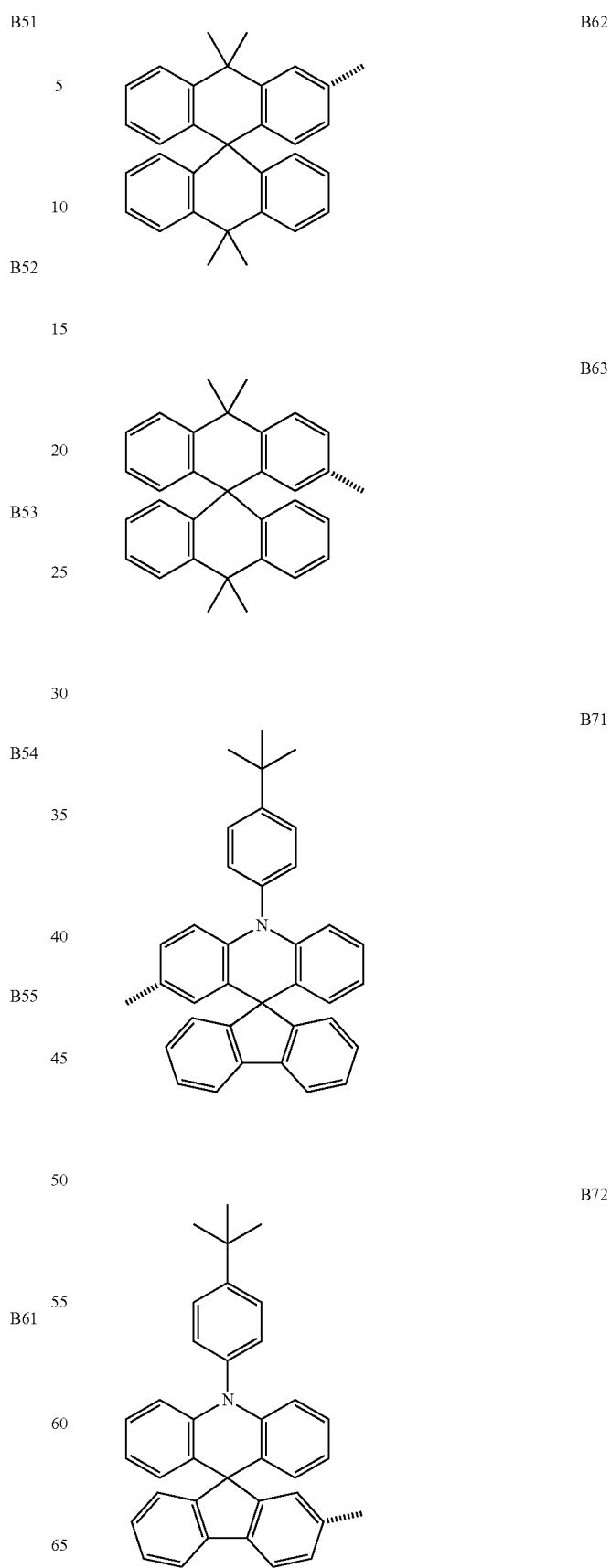

B81

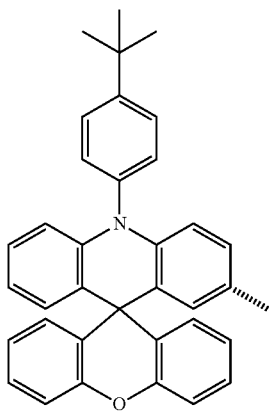

B82

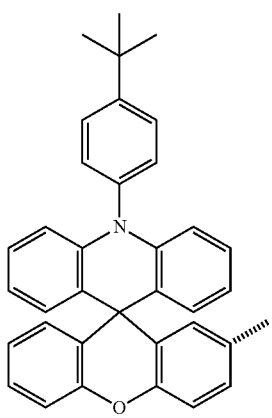

B83

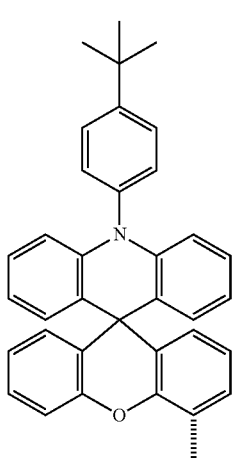

B91

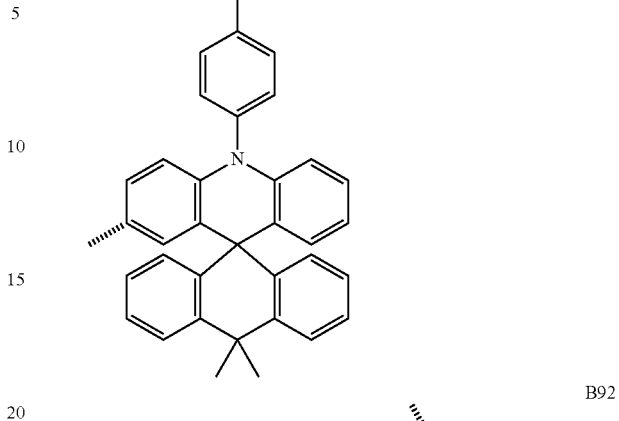

B92

B93

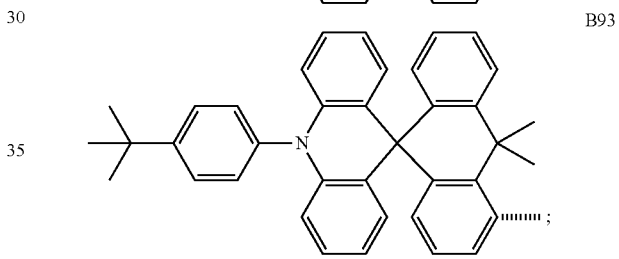

Step S2, cooling the first reaction solution to a second temperature to obtain a mixture; and Step S3, separating the hole transport material from the mixture, the hole transport material including a compound having a general chemical structural formula shown in Formula 1:

AN-BMN        Formula 1.

According to an embodiment of the present invention, the first temperature ranges from 80° C. to 150° C., and the first time period ranges from 12 hours to 36 hours.

According to an embodiment of the present invention, the second temperature is room temperature.

According to an embodiment of the present invention, in the step S1, the organic solvent is toluene, the alkali is sodium tert-pentyloxylate, and the catalyst includes a palladium catalyst and phosphine ligand catalyst.

According to an embodiment of the present invention, the step S2 further includes: subjecting the first reaction solution to extraction, water washing, dehydration, filtration, and centrifugal drying to obtain the mixture.

According to an embodiment of the present invention, in the step S3, the separating is performed by column chromatography with an eluent of dichloromethane and n-hexane in a volume ratio of 1:3.

According to an embodiment of the present invention, in the step S1, the catalyst includes palladium acetate and tri-tert-butylphosphine tetrafluoroborate, and the compound AN-BMN has any one of the following chemical structural formulas:

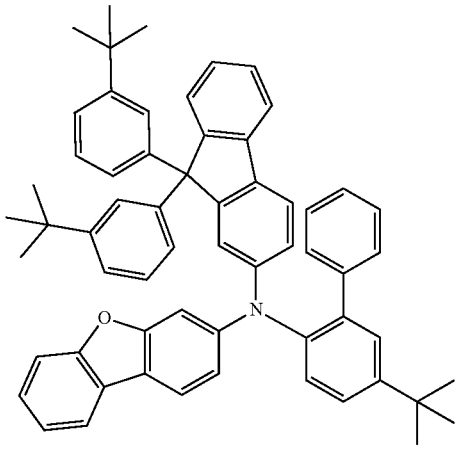

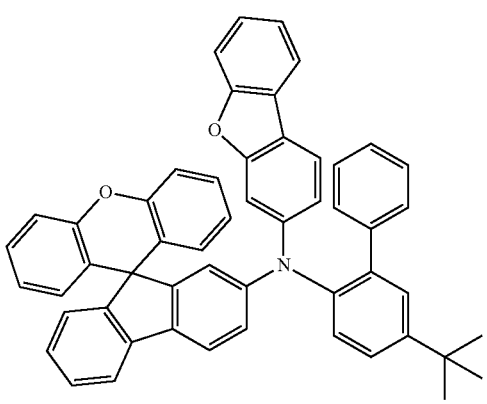

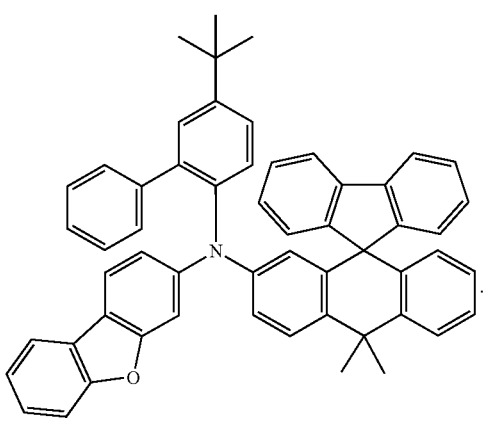

Example 1

In Example 1 of the present invention, the target hole transport material to be synthesized includes Compound 1 of the following chemical structural Formula 2:

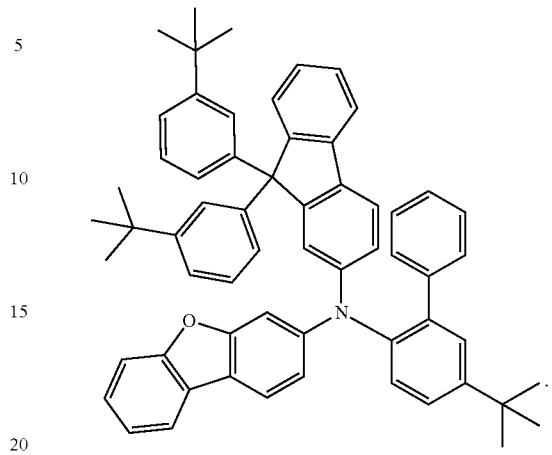

Formula 2

Compound 1 of Formula 2 was synthesized by a reaction based on a synthetic route shown in Reaction Scheme 1:

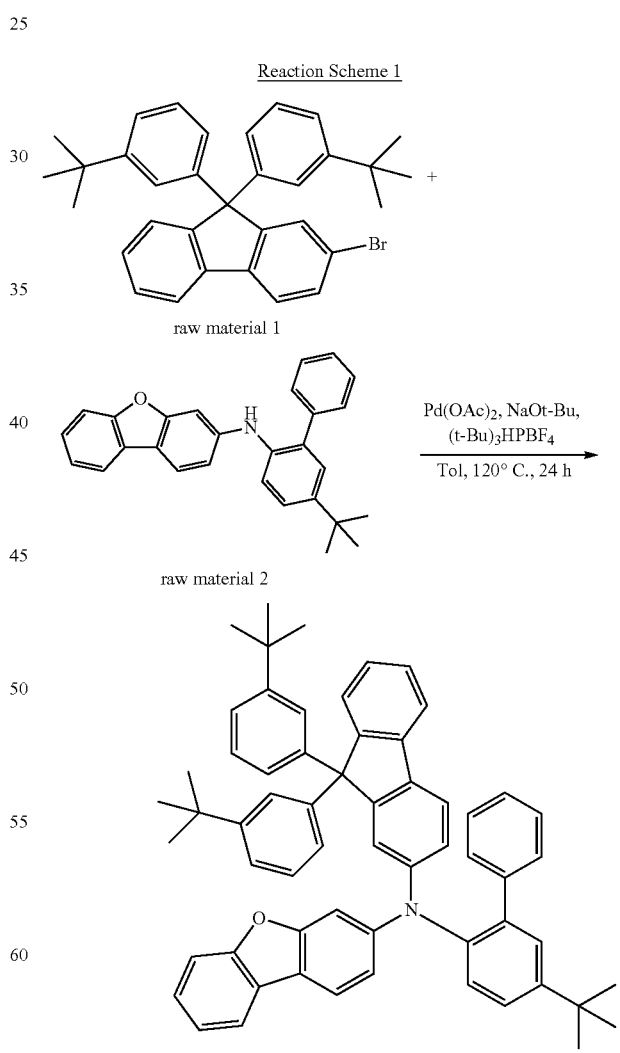

Reaction Scheme 1 raw material 1 raw material 2

Compound 1

The detailed steps of synthesizing Compound 1 are as follows:

The raw material 1 (2.54 g, 5 mmol), the raw material 2 (2.35 g, 6 mmol), palladium acetate (0.09 g, 0.4 mmol), and tri-tert-butylphosphine tetrafluoroborate (0.34 g, 1.2 mmol) were added to a 250 mL two-necked flask, followed by adding sodium tert-amyloxylate (NaOt-Bu, 0.58 g, 6 mmol) thereto in a glove box, then 100 mL of toluene that has been dehydrated and deoxygenated was added to the 250 mL two-necked flask under an argon atmosphere, to perform a reaction at 120° C. for 24 hours, followed by cooling to room temperature. Next, the reaction solution was poured into 200 mL of ice water and extracted three times with dichloromethane. The organic extracts were combined and spun dried, and then purified by silica gel column chromatography (dichloromethane:n-hexane, v:v, 1:3), to obtain 3.0 g of white powder with a yield of 79%. MS (EI) m/z: [M]+: 819.40.

Example 2

In a specific Example 2 of the present invention, the target hole transport material to be synthesized includes Compound 2 of the following chemical structural Formula 3:

Formula 3

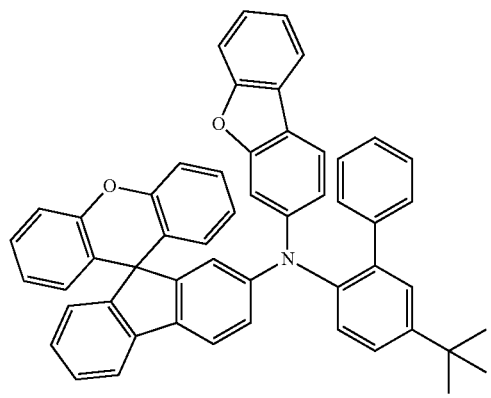

Compound 2 of Formula 3 was synthesized by a reaction based on a synthetic route shown in Reaction Scheme 2:

Reaction Scheme 2

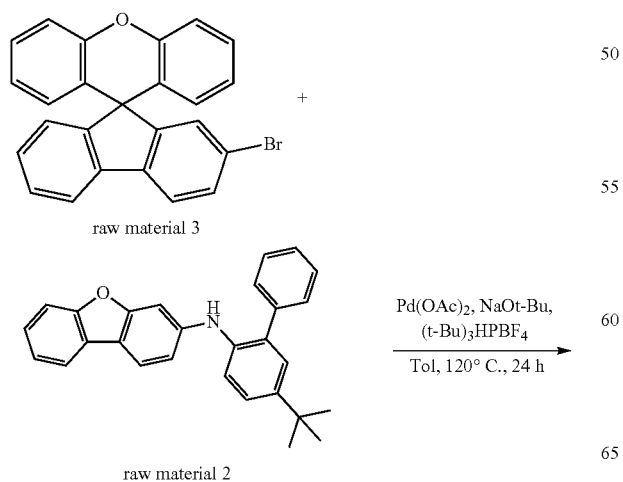

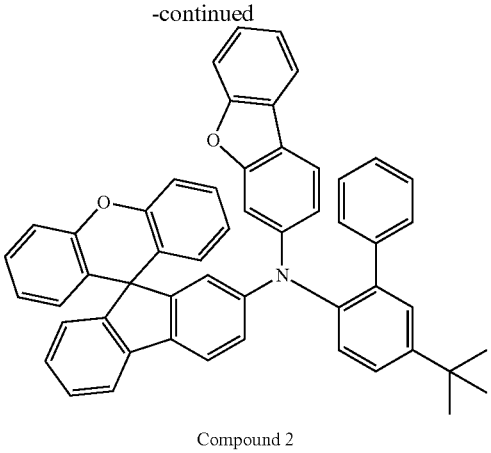

Compound 2

The detailed steps of synthesizing the Compound 2 are as follows:

The raw material 3 (2.05 g, 5 mmol), the raw material 2 (2.35 g, 6 mmol), palladium acetate (0.09 g, 0.4 mmol), and tri-tert-butylphosphine tetrafluoroborate (0.34 g, 1.2 mmol) were added to a 250 mL two-necked flask, followed by adding sodium tert-amyloxylate (NaOt-Bu, 0.58 g, 6 mmol) thereto in a glove box, then 100 mL of toluene that has been dehydrated and deoxygenated was added to the 250 mL two-necked flask under an argon atmosphere, to perform a reaction at 120° C. for 24 hours, followed by cooling to room temperature. Next, the reaction solution was poured into 200 mL of ice water and extracted three times with dichloromethane. The organic extracts were combined and spun dried, and then purified by silica gel column chromatography (dichloromethane:n-hexane, v:v, 1:3), to obtain 2.5 g of white powder with a yield of 69%. MS (EI) m/z: [M]+: 721.10.

Example 3

In a specific Example 3 of the present invention, the target hole transport material to be synthesized includes Compound 3 of the following chemical structural Formula 4:

Formula 4

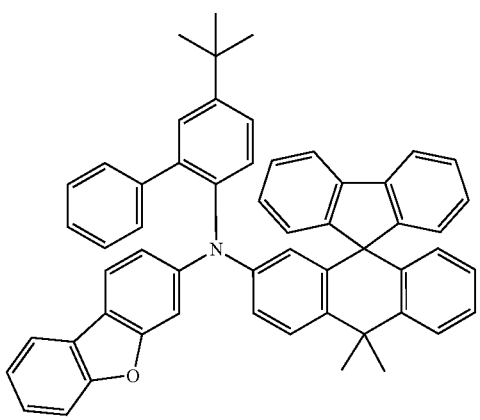

Compound 3 of Formula 4 was synthesized by a reaction based on a synthetic route shown in Reaction Scheme 3:

Reaction Scheme 3

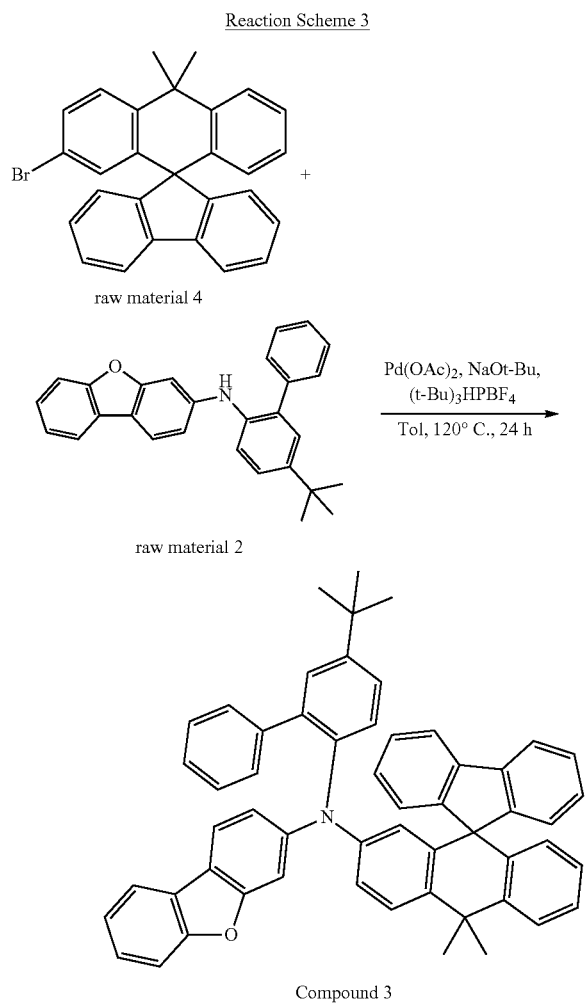

The raw material 4 (2.18 g, 5 mmol), the raw material 2 (2.35 g, 6 mmol), palladium acetate (0.09 g, 0.4 mmol), and tri-tert-butylphosphine tetrafluoroborate (0.34 g, 1.2 mmol) were added to a 250 mL two-necked flask, followed by adding sodium tert-amyloxylate (NaOt-Bu, 0.58 g, 6 mmol) thereto in a glove box, then 100 mL of toluene that has been dehydrated and deoxygenated was added to the 250 mL two-necked flask under an argon atmosphere, to perform a reaction at 120° C. for 24 hours, followed by cooling to room temperature. Next, the reaction solution was poured into 200 mL of ice water and extracted three times with dichloromethane. The organic extracts were combined and spun dried, and then purified by silica gel column chromatography (dichloromethane:n-hexane, v:v, 1:3), to obtain 2.7 g of white powder with a yield of 72%. MS (EI) m/z: [M]+: 747.20.

Specifically, Compound 1, Compound 2, and Compound 3 were determined to have chemical structures of Formula 3, Formula 4, and Formula 5, respectively, and the energy levels of the highest occupied molecular orbital (HOMO) and the lowest unoccupied molecular orbital (LOMO) of Compound 1, Compound 2, and Compound 3 were analyzed and shown in Table 1:

TABLE 1

|  | HOMO (eV) | LUMO (eV) |
|---|---|---|
| Compound 1 | −5.56 | −2.53 |
| Compound 2 | −5.57 | −2.51 |
| Compound 3 | −5.56 | −2.55 |

It can be seen from Table 1 that the hole transport material prepared by using Compound 1, Compound 2, and Compound 3 of the present invention can meet the requirements for the hole transport layer of an electroluminescent device.

In addition, an embodiment of the present invention also provides an electroluminescent device including the above-mentioned hole transport material.

Referring to FIG. 1, specifically, the electroluminescent device 100 includes a substrate 1; a hole injection layer 2 disposed on the substrate 1; a hole transport layer 3 disposed on the injection layer 2; an electron blocking layer 4 disposed on the hole transport layer 3; a light-emitting layer 5 disposed on the electron blocking layer 4; a hole blocking layer 6 disposed on the light-emitting layer 5; an electron transport layer 7 disposed on the hole blocking layer 6; an electron injection layer 8 disposed on the electron transport layer 7; an electrode layer 9 disposed on the electron injection layer 8; and a light-coupling output layer 10 disposed on the electrode layer 9, wherein the hole transport layer 3 includes the above-mentioned hole transport material.

Specifically, Device 100, Device 200, and Device 300 were manufactured by using Compound 1, Compound 2, and Compound 3 as the hole transport layers 3, respectively, and performances of Device 100, Device 200, and Device 300 were measured, wherein the current-brightness-voltage characteristics of the devices were measured by a Keithley source measurement system (Keithley 2400 Sourcemeter, Keithley 2000 Currentmeter) with a calibrated silicon photodiode, and the electroluminescence spectrum was measured by a French JY SPEX CCD3000 spectrometer, and all measurements were performed at room temperature in the atmosphere. The measured performances of Device 100, Device 200, and Device 300 are shown in Table 2, from which, it can be known that the performances of Device 100, Device 200, and Device 300 meet the requirements.

TABLE 2

| Device | hole transport layer | highest current efficiency (cd/A) | (CIEx, CIEy) | maximum external quantum efficiency (%) |
|---|---|---|---|---|
| Device 100 | Compound 1 | 48.6 | (0.683, 0.290) | 39.6% |
| Device 200 | Compound 2 | 47.8 | (0.685, 0.293) | 37.0% |
| Device 300 | Compound 3 | 49.1 | (0.686, 0.295) | 41.0% |

Accordingly, embodiments of the present invention provide a hole transport material, a method of preparing the same, and an electroluminescent device. Through ingenious molecular design, a xanthracene structure is combined with different electron-donating groups to synthesize a series of hole transport materials with a suitable highest occupied molecular orbital (HOMO) energy level and a suitable lowest unoccupied molecular orbital (LUMO) energy level, and a series of high-performance display devices can be manufactured using the hole transport materials provided by the present invention.

While the invention has been described by way of example and in terms of the preferred embodiments, it is to be understood that the invention is not limited to the disclosed embodiments. To the contrary, it is intended to cover various modifications and similar arrangements. Therefore, the scope of the appended claims should be accorded the broadest interpretation so as to encompass all such modifications and similar arrangements.

What is claimed is:

1. A hole transport material, comprising a compound consisting of a donor AN and an acceptor B, the compound having a general chemical structure as shown in Formula 1:

AN-BMN            Formula 1, wherein the donor AN is selected from any one of the following structural formulas:

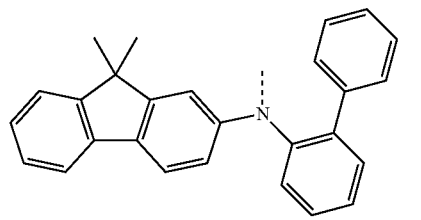
A1

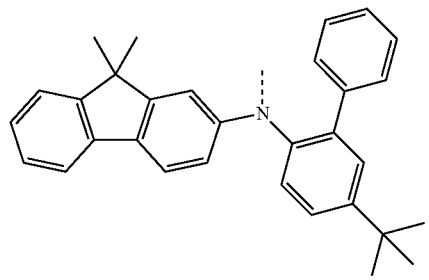
A2

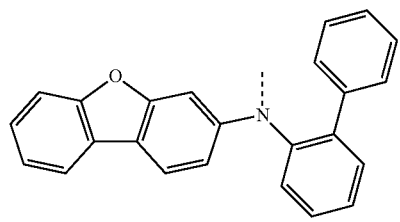
A3

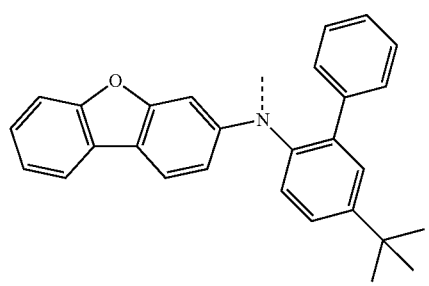
A4

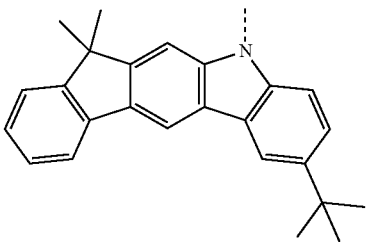
A5

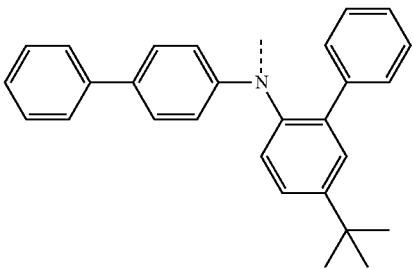
A6

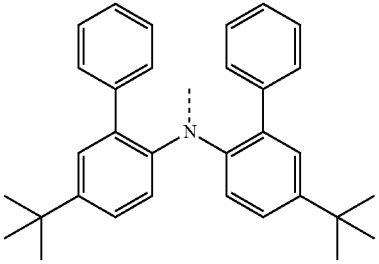
A7

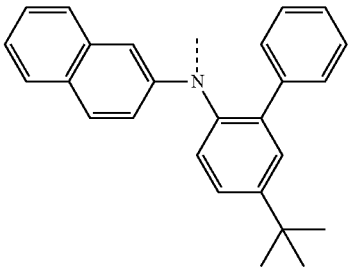
A8

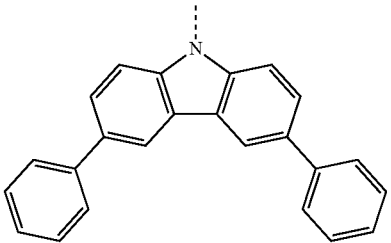
A9

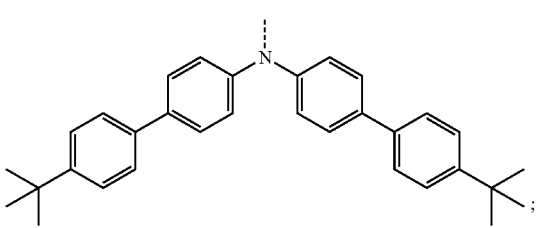
A10 and
the acceptor BMN is selected from any one of the following structural formulas:
B11
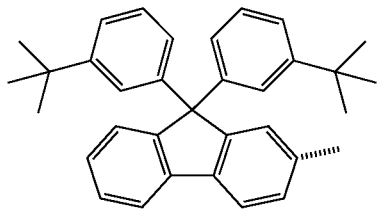
B12
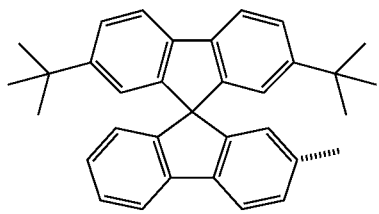
B21
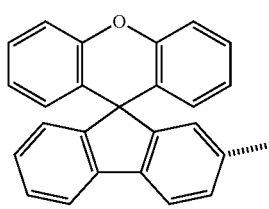
B22
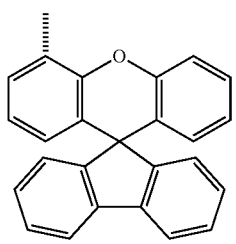
B23
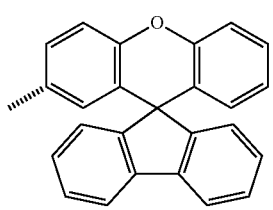
B31
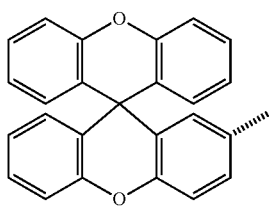
B32
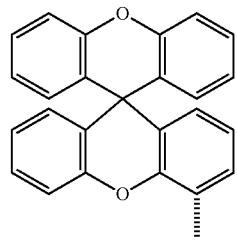
B41
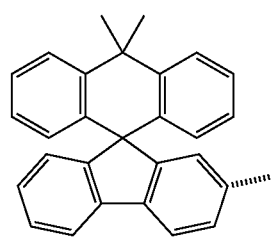
B42
B43
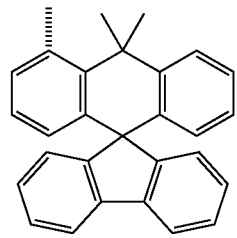
B44
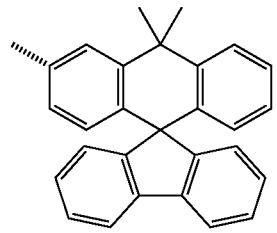
B51

B52 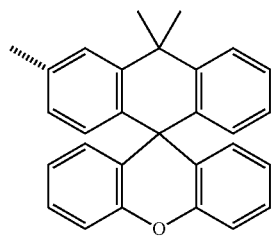
B53 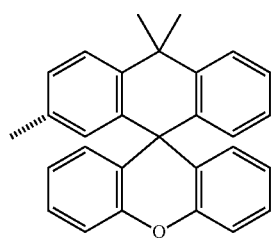
B54 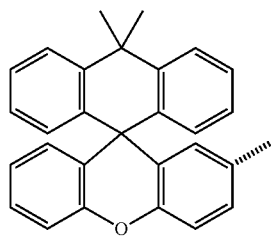
B55 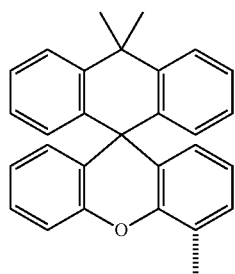
B61 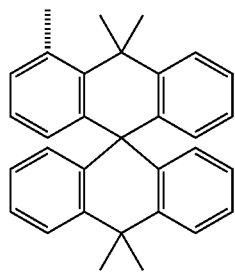
B62 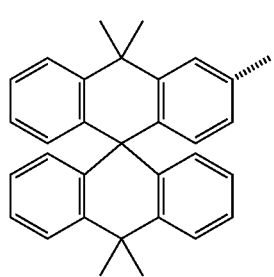
B63 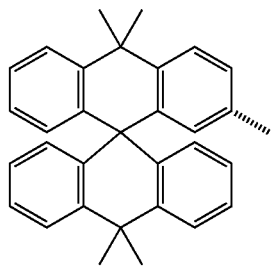
B71 
B72 
B81 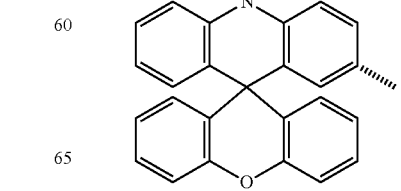

-continued
B82
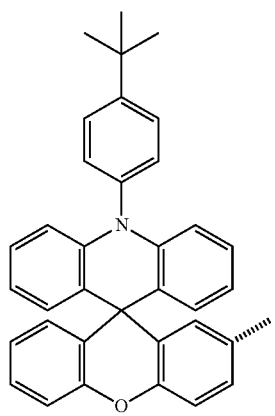
B83
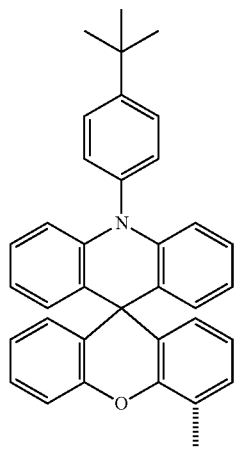
B91
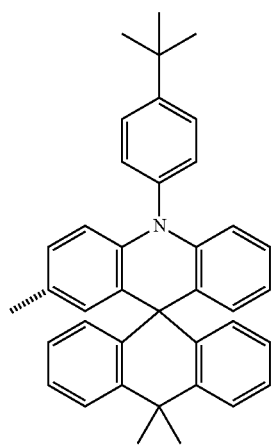
B92
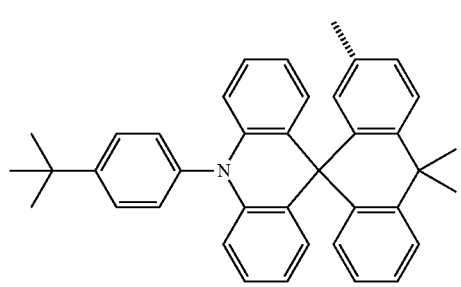
-continued
B93
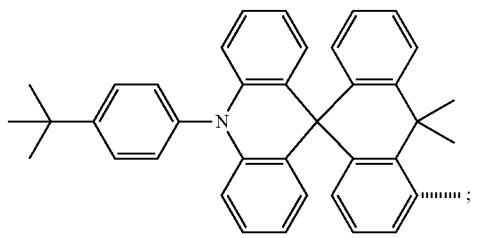
wherein the compound AN-BMN has any one of the following structural formulas:
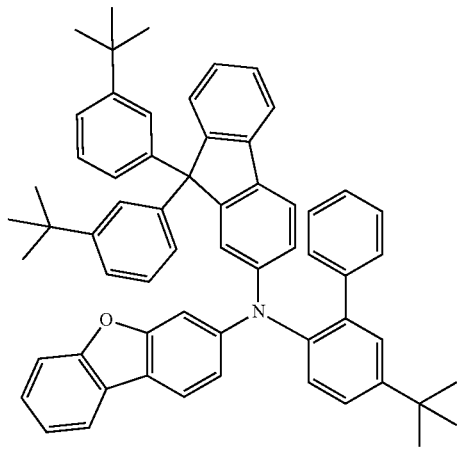
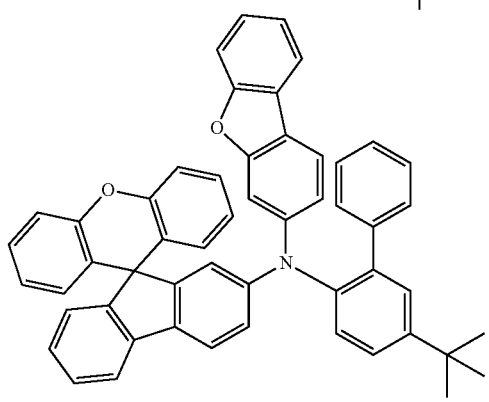
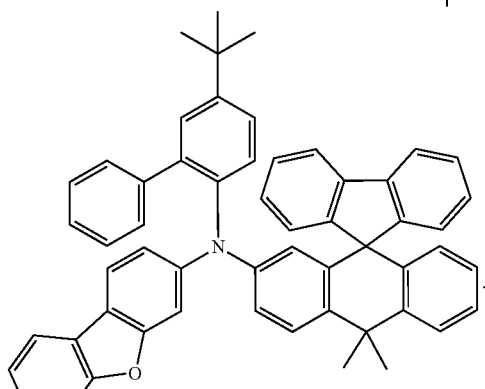
2. A method of preparing a hole transport material, comprising the following steps:

Step S1, adding an acceptor compound BMN-X, a donor compound AN-H, and a catalyst into an organic solvent containing an alkali under an inert gas environment to conduct a reaction for a first time period at a first temperature to obtain a first reaction solution, wherein X is halogen, the donor AN is selected from any one of the following structural formulas:

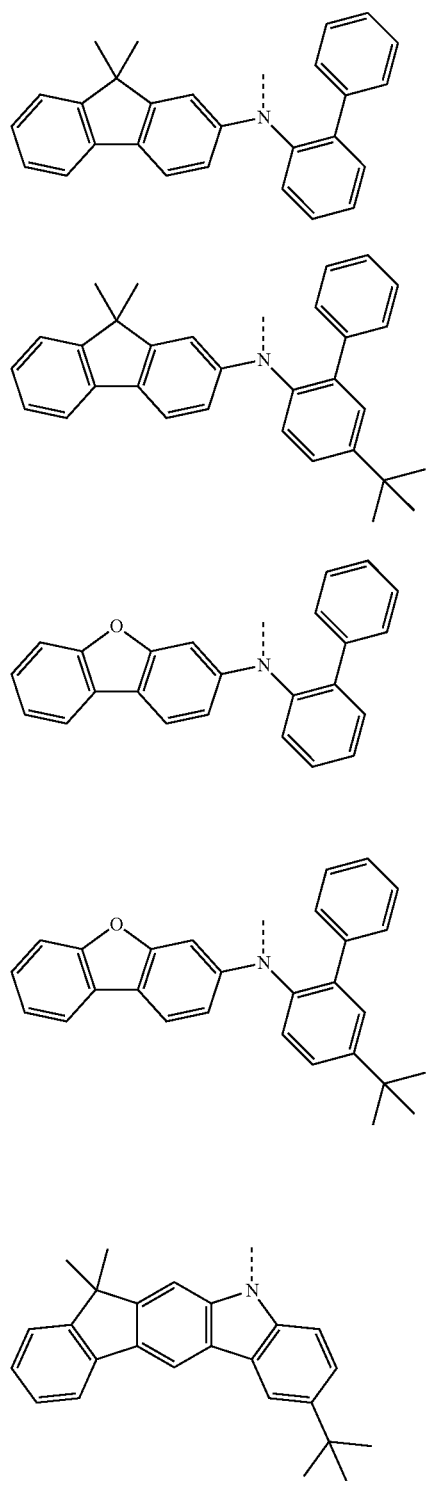

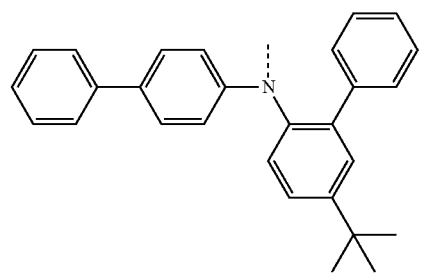

and the acceptor BMN is selected from any one of the following structural formulas:

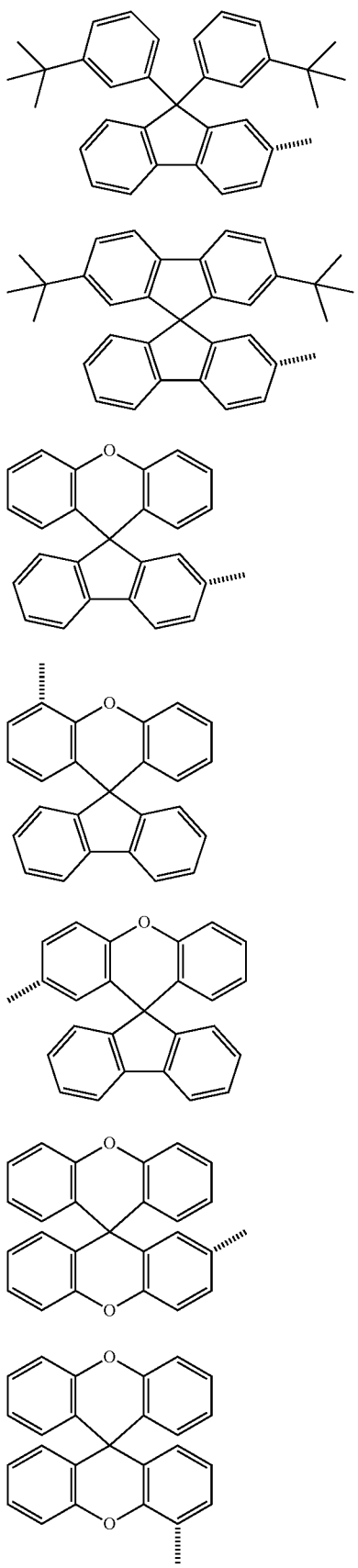
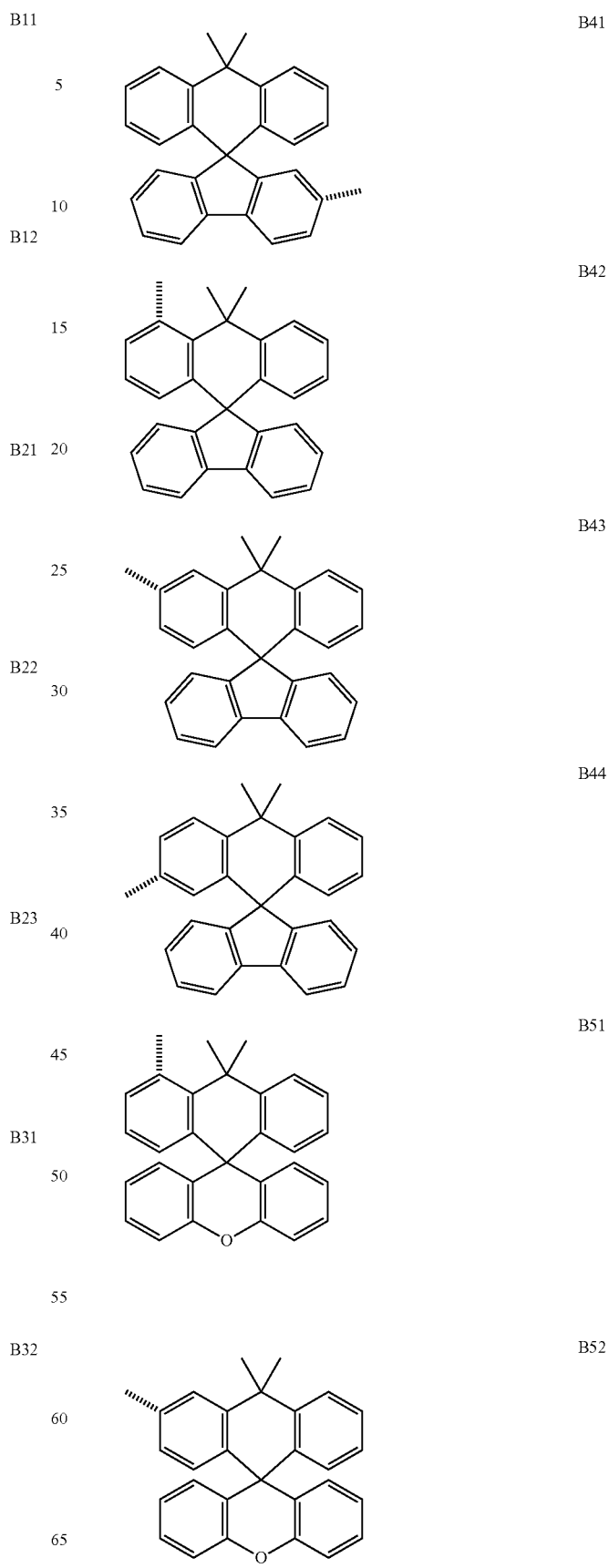

-continued
B53 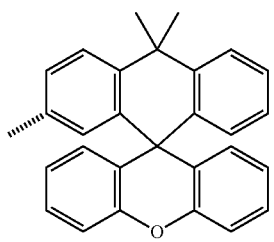
B54 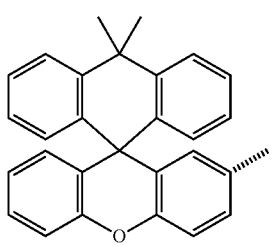
B55 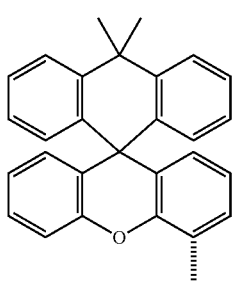
B61 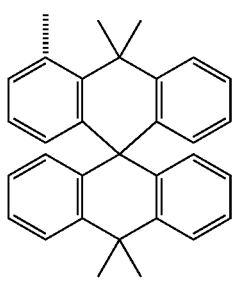
B62 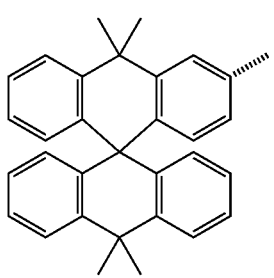
B63 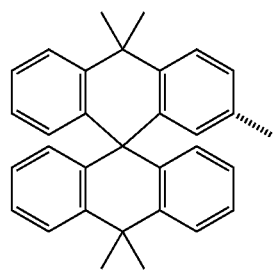
B71 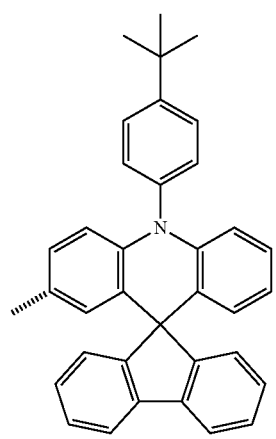
B72 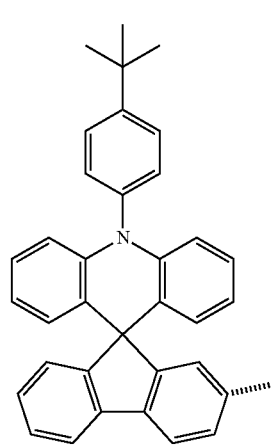
B81 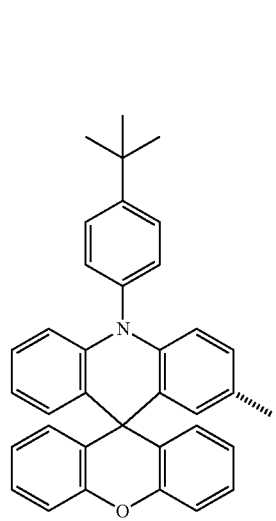

B82
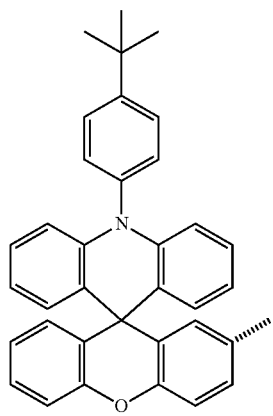
B83
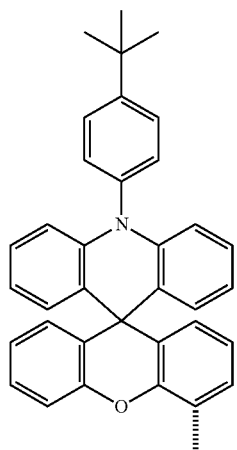
B91
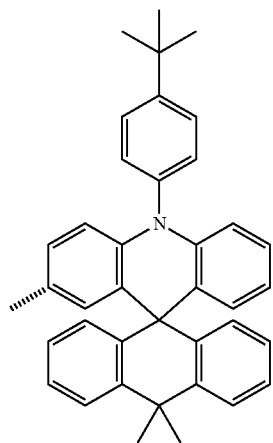
B92
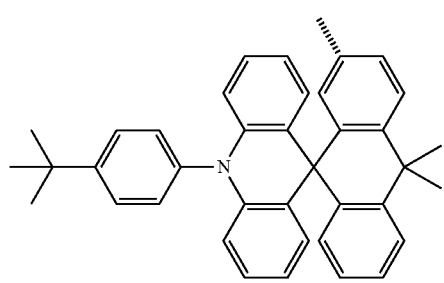
B93
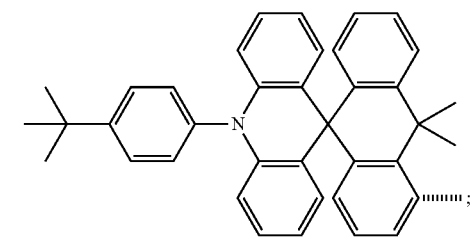
wherein the catalyst comprises palladium acetate and tri-tert-butylphosphine tetrafluoroborate, and the compound AN-BMN has any one of the following structural formulas:
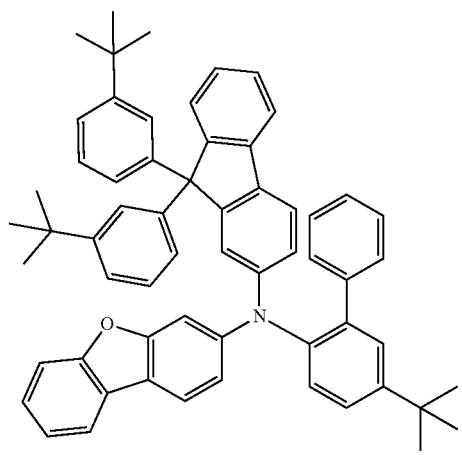
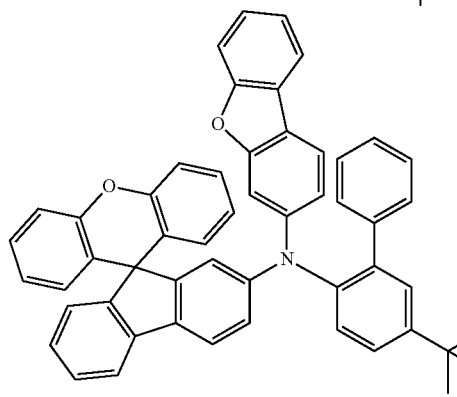
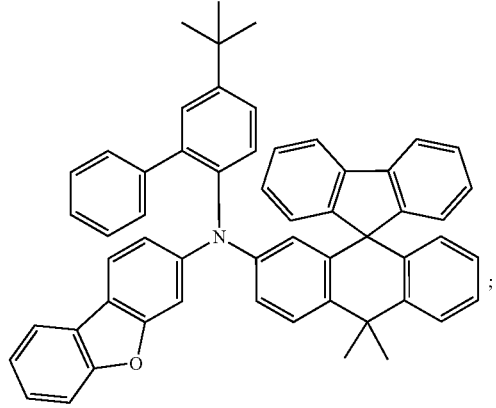

Step S2, cooling the first reaction solution to a second temperature to obtain a mixture; and Step S3, separating the hole transport material from the mixture, the hole transport material comprising a compound having a general chemical structural formula shown in Formula 1:

AN-BMN　　　　　　　　　　　　　　　　Formula 1.

3. The method of preparing the hole transport material according to claim 2, wherein the first temperature ranges from 80° C. to 150° C., and the first time period ranges from 12 hours to 36 hours.

4. The method of preparing the hole transport material according to claim 2, wherein the second temperature is room temperature.

5. The method of preparing the hole transport material according to claim 2, wherein in the step S1, the organic solvent is toluene, the alkali is sodium tert-pentyloxylate, and the catalyst comprises a palladium catalyst and phosphine ligand catalyst.

6. The method of preparing the hole transport material according to claim 2, wherein the step S2 further comprises: subjecting the first reaction solution to extraction, water washing, dehydration, filtration, and centrifugal drying to obtain the mixture.

7. The method of preparing the hole transport material according to claim 2, wherein in the step S3, the separating is performed by column chromatography with an eluent of dichloromethane and n-hexane in a volume ratio of 1:3.

8. An electroluminescent device, comprising:
a substrate;
a hole injection layer disposed on the substrate;
a hole transport layer disposed on the injection layer;
an electron blocking layer disposed on the hole transport layer;
a light-emitting layer disposed on the electron blocking layer;
a hole blocking layer disposed on the light-emitting layer;
an electron transport layer disposed on the hole blocking layer;
an electron injection layer disposed on the electron transport layer;
an electrode layer disposed on the electron injection layer; and
a light-coupling output layer disposed on the electrode layer,
wherein the hole transport layer comprises the hole transport material according to claim 1.

\* \* \* \* \*